United States Patent
Pellegretti et al.

(10) Patent No.: US 10,725,159 B2
(45) Date of Patent: Jul. 28, 2020

(54) METHOD AND SYSTEM FOR PERFORMING RETROSPECTIVE DYNAMIC TRANSMIT FOCUSSING BEAMFORMING ON ULTRASOUND SIGNALS

(71) Applicant: ESAOTE SpA, Genoa (IT)

(72) Inventors: Paolo Pellegretti, Genoa (IT); Marco Crocco, Ovada (IT)

(73) Assignee: ESAOTE S.p.A., Genoa (IT)

(*) Notice: Subject to any disclaimer, the term of this patent is extended or adjusted under 35 U.S.C. 154(b) by 294 days.

(21) Appl. No.: 15/637,129

(22) Filed: Jun. 29, 2017

(65) Prior Publication Data

US 2018/0003811 A1 Jan. 4, 2018

(30) Foreign Application Priority Data

Jun. 30, 2016 (EP) ..................... 6177117

(51) Int. Cl.
*G01S 7/52* (2006.01)
*G01S 15/89* (2006.01)
(Continued)

(52) U.S. Cl.
CPC ........ *G01S 7/52095* (2013.01); *A61B 8/5207* (2013.01); *A61B 8/54* (2013.01);
(Continued)

(58) Field of Classification Search
CPC ............. G01S 7/52095; G01S 15/8915; G01S 15/8918; G01S 15/8927; A61B 8/5207
See application file for complete search history.

(56) References Cited

U.S. PATENT DOCUMENTS 5,127,409 A 7/1992 Daigle
6,685,645 B1 * 2/2004 McLaughlin ............ A61B 8/08
600/447

(Continued)

OTHER PUBLICATIONS

Bradley, Chuck, "Retrospective Transmit Beamformation", ACUSON SC2000, Volume Imaging Ultrasound System, Aug. 2, 2008 (Aug. 2, 2008), XP055329983, Retrieved from the Internet on Dec. 16, 2016: RL: https://www.siemens.com.tr/i/Assets/saglik/Whitepaper_Bradley.pdf.

(Continued)

*Primary Examiner* — Ian J Lobo
(74) *Attorney, Agent, or Firm* — Dickinson Wright PLLC

(57) ABSTRACT

Performing retrospective dynamic transmit focusing beamforming for ultrasound signals by a) transmitting plural transmit beams, each transmit beam centered at a different position along array, having width or aperture encompassing plural laterally spaced line positions, each transmit beam width or aperture overlapping width or aperture of adjacent transmit beam or more laterally spaced transmit beams; b) receiving echo signals; c) processing echo signals to produce plural receive lines of echo signals at laterally spaced line positions within width or aperture of transmit beam; d) repeating steps b), (c) for additional transmit beams of plural transmitted transmit beams; e) equalizing phase shift variance among receive lines at common line position resulting from transmit beams of different transmit beam positions concurrently with steps c), d); f) combining echo signals of receive lines from different transmit beams spatially related to common line position to produce image data; g) produces an image using image data.

14 Claims, 14 Drawing Sheets

(51) Int. Cl.
*A61B 8/00* (2006.01)
*A61B 8/08* (2006.01)

(52) U.S. Cl.
CPC ...... *G01S 15/8915* (2013.01); *G01S 15/8918* (2013.01); *A61B 8/4483* (2013.01); *G01S 15/8927* (2013.01)

(56) References Cited

U.S. PATENT DOCUMENTS

| 8,137,272 | B2 | | 3/2012 | Cooley et al. | |
|---|---|---|---|---|---|
| 9,345,455 | B2 | | 5/2016 | Burcher et al. | |
| 2005/0131302 | A1 | * | 6/2005 | Poland | A61B 8/14 600/459 |
| 2009/0069693 | A1 | * | 3/2009 | Burcher | G01S 7/52028 600/459 |
| 2009/0306512 | A1 | | 12/2009 | Loftman | |
| 2013/0041252 | A1 | * | 2/2013 | Vignon | A61B 8/0841 600/424 |
| 2015/0049578 | A1 | * | 2/2015 | Hoctor | G01S 7/52046 367/7 |

OTHER PUBLICATIONS

European Search Report dated Dec. 19, 2016 issued in EP Patent Application No. 16177117.5.

\* cited by examiner

Fig. 3A PRIOR ART

TX 1,
TX 2,
TX - RX lag: l=0
TX - RX lag l = 4
Channel n
Channel n $$B_p = \sum_l B_l \left( \frac{2\|p\|}{c} - \frac{\|p - p_l\|}{c} \right)$$

RTB delay 320

METHOD AND SYSTEM FOR PERFORMING RETROSPECTIVE DYNAMIC TRANSMIT FOCUSSING BEAMFORMING ON ULTRASOUND SIGNALS

BACKGROUND OF THE INVENTION

Ultrasound systems exist today that utilize a variety of techniques for processing ultrasound signals to generate information of interest. For example, a variety of techniques exist today for performing beamforming upon ultrasound receive signals.

One approach to beamforming performs so called Retrospective Transmit Beamformation (RTBF). This is a transmit focusing technology that achieves dynamic focusing by performing the transmit focusing operation retrospectively.

In Retrospective Transmit Beamforming (RTB), following a transmission event of an ultrasound transmit beam, multiple receive beams are generated. Ultrasound images are composed of a set of lines along each one of which the image system acquires image data until a full frame has been scanned.

Retrospective Transmit Beamforming uses a high parallel line acquisition scheme in which following each transmit event of a transmit beam multiple receive beams are simultaneously acquired in parallel along different lines.

According to this technique, the transmit beam is generated with a width that encompasses multiple receive lines. Generally, this can be achieved by transmitting from a small transmit aperture, for example by transmitting using a lesser number of elements of an array of transducers that the total number of transducer provided in the array. Following transmission, echoes are received which are focused along each line of the lines encompassed by the width of the transmitted beam. Focusing is obtained by delaying and summing the echoes received by the transducer elements of the receive aperture so that for generating the image of each line of the multiple lines encompassed by the width of the transmit beam, only the contribution of coherent signals along each different line location are used.

For scanning the entire image frame and acquiring all the image lines needed for generating the image, further transmit beams are transmitted by shifting the transmit aperture laterally in one direction relatively to the transmit aperture of the previous transmit event.

Lateral shift is carried out in such a way that the two adjacent transmit apertures overlap so that at least some of the receive lines encompassed by the width of a first transmit beams are also encompassed by the width of at least one or more of the following transmit beams which aperture has been progressively laterally shifted in relation to the transmit aperture of the first transmit beam.

As a result, depending on the transmit aperture of the transmission, i.e. of the number of lines encompassed by the width of the transmit beam and on the lateral shift step of the transmit aperture for each following transmit event, lines of image data along each receive line is formed by co-aligned beams along the said receive line which are combined together.

Transmission and reception continues across the image field in this manner until the full image field has been scanned. Each time the maximum number of receive lines for a given line location has been acquired, the receive lines are processed together to produce a line of image data at that location.

Due to the fact that each receive signal contributing to the same image line data at a certain receive line location derives from a transmit beam whose transmit aperture has been shifted with respect to the other transmit beams, the said receive signals contributing to the same line data are not coherent and there is the need of equalizing the phase shift variance that exists from line to line for the multilines with differing transmit-receive beam location combinations, so that signal cancellation will not be caused by phase differences of the combined signals.

In U.S. Pat. No. 8,137,272 a method and an ultrasound apparatus are disclosed which operates according to the above RTB technique.

U.S. Pat. No. 8,137,272 suggests a method for producing an ultrasound image with an extended focal range, comprising the steps of:

transmitting a plurality of transmit beams from an array transducer, each transmit beam being centered at a different position along the array and each transmit beam encompassing a plurality of laterally spaced line positions which are spatially related to laterally spaced line positions of another beam;

receiving echo signals with the array transducer;

concurrently processing the echo signals received in response to one transmit beam to produce a plurality of receive lines of echo signals at the laterally spaced line positions of the beam;

repeating the concurrently processing for additional transmit beams;

equalizing the phase shift variance among receive lines at a common line position resulting from transmit beams of different transmit beam positions;

combining echo signals of receive lines from different transmit beams which are spatially related to a common line position to produce image data; and producing an image using the image data.

According to this solution the array transducer elements are connected to a multiline receive beamformer which produces a plurality of receive lines at a plurality of corresponding line positions in response to one transmit beam at each one of a certain number of different beam locations. The multiline receive beamformer operates by using the traditional beamforming technique, namely the so called delay and sum in which the delays are determined by the relative position of the focal point of the transmit beam, the points on the receive line and the transducer position in the array. These delays are determined for all the multiline beamformers along each receiving line according to the same fixed rules which only depend on the time of arrival of the echoes from a reflecting point at a certain transducer element of an array of transducer elements.

So the traditional beamforming delays are based merely on the relative position of the reflecting point and of each of the transducer elements.

The step of equalizing the phase shift variance among receive lines at a common line position resulting from transmit beams of different transmit beam positions is carried out separately from beamforming at a later step. Equalizing further comprises relatively delaying the signals of receive lines along a common line position obtained from different transmit beams prior to combining these receive line signals together in order to receive a beamformed receive data along a certain line position.

According to this method the receive echoes relating to the same line position are firstly selected and summed by the delay and sum process of the multiline beamformer, irrespectively of the possible phase shifts introduced by the shift of the transmit aperture between the beams of the sequence of transmit events.

In a following step the phase shift of the receive signals for the same line location is equalized by a further delay which is determined as a function of the step of lateral shift of the transmit aperture between the transmit events, since the multiple receive signals along the same line position which has to be combined are obtained each one by a transmit beam which has been laterally shifted relatively to the receive line position.

Also a further weighting step of the signals of the receive lines from different transmit beams prior to combining is carried out in a separate step after multiline beamforming.

FIG. 2 shows a system according to the prior art U.S. Pat. No. 8,137,272 and FIG. 3A shows the effect of the equalizing step of the phase shift variance among receive lines at a common line position resulting from transmit beams of different transmit beam positions according to U.S. Pat. No. 8,137,272 and the method and system disclosed therein.

A transducer array comprising a number N of transducer elements of an ultrasound probe is driven by a transmit beamformer in such a way that selected groups of the transducer elements are actuated at respectively delayed times to transmit beams focused at different focal regions along the array. The echoes received by each transducer element of the array in response to each transmit beam are applied to the inputs of a multiline beamformer comprising multiline processors 210a-210k. Each multiline processor 210a-210k processes the each of the k parallel receive lines encompassed by every transmit beam. Each multiline processor comprises a receive beamformer which applies delays 202 and, if desired, apodization weights. The outputs of the multiline processors 210a-210k are coupled to a line memory 212 which stores the received multilines until all of the R multilines needed to form a line of display data have been acquired. The group of multilines used to form a particular line of display data are applied to respective ones of multipliers 216a-216R to produce the display data for the corresponding line location. The echo data from each line may, if desired be weighted by apodization weights 214a-214R. The echoes from each line are weighted by the multipliers 216a-216R and delayed by delay lines 218a-218R. The delays are used to equalize the phase shift variance that exists from line to line for the multilines with differing transmit-receive beam location combinations, so that signal cancellation will not be caused by phase differences of the combined signals. Due to the fixed geometry of the Rx and TX paths and of the lateral shift steps of the transmit aperture in relation to the geometry of the transducer array the delays can be calculated in real time or even calculated in advance and stored in a memory, for example in the former of a table 228.

The delay 218 and a summer 220 effect a refocusing of the signals received from the several receive multilines which are co-aligned in a given direction. The refocusing adjusts for the phase differences resulting from the use of different transmit beam locations for each multiline, preventing undesired phase cancellation in the combined signals.

In FIG. 3A the wavefront of two following transmission events TX1 and TX2 are shown. The transmit aperture of TX2 has been shifted laterally to the right in respect to TX1 by a step corresponding to the dimension of four transducer elements 301 of a transducer array 300. The situation is illustrated in relation to the n-th transducer element as receiving element.

The two wavefronts WF1 and WF2 are in general not planar and a focus P on a receiving line coincident with the center line of the transmission beam the path TX is considered.

According to an embodiment herein the wavefronts are spherical or nearly spherical.

The echoes generated at P has to travel a path RX to reach the n-th transducer element. The Second transmit event generates a wavefront WF2 which reaches the point with a different phase due to the lateral shift of the transmit beam of the transmit event TX2.

As it appears clearly, the receive multiline beamforming delays are defined by the geometry determined by the position of each focus points along each line at each line location relatively to the position of the transducer elements of the transducer array.

The equalization process would require to compensate for the delay of the transmit beam having the wavefront WF2 in reaching the focus points P on the corresponding line, which in FIG. 3A is indicated as RTB delay and is represented by the difference 320 in position of the focus point P of the transmit beam TX1 and the point P1.

In FIG. 4 the effect of the equalization process obtained by the known technique is illustrated schematically.

Considering $B_p$ the beam signal related to focal point p and $S_{l,n}(t)$ the signal at the probe channel n, i.e. at the n-th transducer element of the transducer array 300, which is related to a difference "l" in line position between the transmit center line of a second or following transmit beam TX2 and a receive line, then the beam signal can be described by the following equation:

$$B_p = \sum_l B_l\left(\frac{2\|p\|}{c} - \frac{\|p - p_l\|}{c}\right)$$

Where c is the speed of sound and $$t_p = \frac{2\|p\|}{c}$$

is the time at which the beam signal is focalized at point p, for l=0, which means for coincident center line of the transmit beam TX1 and receive line of the echoes.

The term $$\frac{\|p - p_l\|}{c}$$

defining the delay in reaching the point p of the wave front of the transmit beam according to the l-th shift of the transmit aperture relatively to the transmit beam focused at p in a transmit event in which the receive line is coincident with the transmit beam center line and which is defined above as RTB delay 220.

Further expanding the above equation $$B_p = \sum_l B_l\left(\frac{\|p\|}{c} + \frac{\|p_l\|}{c}\right) = \sum_l \sum_n s_{l,n}\left(\frac{\|\hat{p}_l\|}{c} + \frac{\|\hat{p}_l - n\|}{c}\right)$$

By using the relation $$\hat{p}_l = \frac{p + p_l}{2}$$

it appears clearly that the term $$\frac{\|\hat{p}_l\|}{c}$$

is the transmission beam path and the term $$\frac{\|\hat{p}_l - n\|}{c}$$

is the RX path to the nth transducer element of the transducer array.

It has to be noted that in the example of FIGS. 3A and 3B the easiest case has been illustrated in which the receive line RX coincides with the centreline of the first transmit beam of the plurality of laterally shifted transmit beams, so that the distance "l" or the lateral shift step of the centreline of the following or second transmit beam TX2 from the receive line is identical with the lateral shift step between the centre lines of the first and of the second transmit beams TX1, TX2.

As it is shown in FIG. 3B, the effect of the equalisation plus focalization in reception according to the prior art is equivalent, in terms of applied delays in reception, to a traditional focalization by means of the beamforming delays at a point $\hat{p}_1$ which is half way between point p and point $p_1$. In this case the phase shift introduced by the shifting of the transmit aperture is not exactly compensated. In particular, the focalization delays in reception are computed relatively to the point $\hat{p}_1$, while the physical propagation delays in reception are proportional to the distance between point P and each transducer n. Therefore, the propagation delays relative to signal backscattered from point P are not exactly compensated by focalization delays applied in reception.

SUMMARY

In accordance with embodiments herein, a method is provided for performing retrospective dynamic transmit focusing beamforming for ultrasound signals. The method comprises The method comprises the steps of:
a) transmitting a plurality of transmit beams from an array transducer, each transmit beam being centered at a different position along the array and each transmit beam having a width or an aperture encompassing a plurality of laterally spaced line positions, each transmit beam width or aperture overlapping at least partially at least the width or the aperture of the immediately adjacent transmit beam or of more laterally spaced transmit beams;
b) receiving echo signals with the array transducer;
c) processing the echo signals received in response to one transmit beam to produce a plurality of receive lines of echo signals at the laterally spaced line positions within the width or the aperture of the transmit beam;
d) repeating the receiving step b) and the processing step c) for the additional transmit beams of the plurality of transmitted transmit beams of step a);
e) equalizing the phase shift variance among receive lines at a common line position resulting from transmit beams of different transmit beam positions;
f) combining echo signals of receive lines from different transmit beams which are spatially related to a common line position to produce image data; and g) producing an image using the image data;
and in which the step e) of equalizing the phase shift is carried out concurrently with in the processing step c) and d).

According to an embodiment, for each insonification, i.e. for each transmission of a transmit beam with a certain aperture, the received echoes are processed by a set of beamformers, each one related to a different line of sight; each beamformer being characterized by a set of dynamic delays and optionally by a set of apodization weights, which are different for each beamformer.

According to an embodiment the delays are given by the sum of focalization delays and RTB delays, which are the phase shifts between the wave fronts of the different transmit beams centered at different transmission lines at the focal points along one receive line having a certain line location.

According to an embodiment after beamforming each line of sight is stored in a buffer and along with subsequent insonifications, receive lines corresponding to the same line positions are coherently summed together to produce a final beamformed line with uniform spatial resolution.

According to still another embodiment for each receive signals along a receive line position the focalization delays and the phase shift equalization delays are applied to the receive signal contributions of the transducer elements or channels before their summation.

Differently from the retrospective dynamic transmit focusing beamforming according to the prior art in which two stages of the process are provided and carried out one after the other, namely firstly applying standard dynamic focusing on a set of receive lines and subsequently realigning each beamformed line by a proper delay and combining together the delayed lines by a weighted sum, according to embodiments herein beamforming and realignment—i.e. equalization—are performed jointly, by using different delays for each receive beamforming process related to each line in the multiline acquisition. In this way exact focalizations are automatically obtained.

According to a further embodiment, the above method provides for detecting relative image motion and adjusting the aperture of the ultrasound transmit and/or received beam in response to the presence of motion.

An embodiment herein provides for the following steps:
detecting motion of the objects within the image field or ROI;
determining a value representative of motion;
adjusting the transmission and reception of the ultrasound beam increasing or decreasing the lateral width of the ultrasound beam in order to encompass a lower number of lines when motion is present relatively to the number of lines encompassed when motion is absent.

The result of this improvement of the basic method consist in the fact that when motion of the objects in the imaged ROI (region of interest) is detected a smaller transmit beam aperture is used so that the lines which are combined span a shorter period of transmit times.

The result of these adjustments are that a shorter time is needed to acquire the multilines which are to be combined, the shorter time period being less affected by motion than would a longer acquisition interval.

Several different ways of determining a parametric value representative of a measure of the motion may be used. In an embodiment a correlation method can be used in which image pixel values in an identical area of consecutive images are correlated one with the other. The correlation factor obtained is then a measure of the entity of the motion and a threshold value can be defined delimiting an upper and a lower value range for the correlation factor and thus a reduction or an increase of the ultrasound beam aperture.

The correlation factor may be automatically used to determine the aperture variation of the ultrasound beam or it may be printed on a screen for allowing the user to manually change the beamforming according to the aperture. Correlation techniques are disclosed for example in U.S. Pat. No. 5,127,409.

According to still another embodiment, the ultrasound beam aperture either of the transmitted beam or of the received beam is modified by increasing or decreasing the lateral width of the beam so to encompass a lower or a higher number of lines as a function of change in the imaging mode, for example from B-mode to Doppler imaging mode.

The variation of the beam aperture as described in the above embodiment can be set automatically and/or by the user.

Thanks to the above embodiments, the drawbacks are compensated deriving from significant motion, either of materials in the image field or of the probe with respect to the image field. If not taken into account, these motions may cause signal differences which result in cancellation rather than the desired signal reinforcement when the signals deriving from the different transmit beams and relating to the same lines are combined together. This problem is more acute with longer acquisition intervals during which greater numbers of transmit beams are acquired along a same line for combination.

Still according to a further embodiment which may be provided alternatively or in combination with increasing or decreasing the ultrasound beam aperture a step may be carried out in which manually or automatically also the number of lines and or the spacing between the lines is modified as a function of the motion detected.

An embodiment herein provides for a method according to one or more of the previously disclosed combination of steps in which the following steps are carried out:
  detecting motion of the objects within the image field or ROI;
  determining a value representative of motion;
  adjusting the spacing and/or the number of a plurality of laterally spaced apart transmit lines encompassed by the transmit beam width or aperture as a function of the value representative of the detected motion.

According to a further embodiment the number of lines and or the spacing of the receive lines can be modified as a function of the motion detection. Also this variation of the number or of the spacing of the receive lines can be provided alternatively or in combination with the beam aperture variation and/or with the number and or the spacing of the transmit lines.

An embodiment herein provides for a method according to one or more of the previously disclosed combination of steps in which the following steps are carried out:
  detecting motion of the objects within the image field or ROI;
  determining a value representative of motion;
  adjusting the spacing and/or the number of a plurality of laterally spaced apart receive line positions encompassed by the transmit beam aperture as a function of the value representative of the detected motion.

According to embodiments herein, an ultrasound system is provided that comprises:
  an ultrasound probe including an array of transducer elements transforming electric input signals in acoustic transmit signals and transforming acoustic echo signals in electric receive signals;
  a transmit beamformer generating the driving input signals for the transducer elements according to a transmit scheme for driving the transducer array to transmit a plurality of transmit beams from an array transducer, each transmit beam being centered at a different position along the array and each transmit beam having a width or an aperture encompassing a plurality of laterally spaced line positions, each transmit beam width or aperture overlapping at least partially at least the width or the aperture of the immediately adjacent transmit beam or of more laterally spaced transmit beams;
  the transmit beamformer including a memory configured to store time delays to synchronize contributions of transmit signals of the transducer elements of the array according to the said transmission scheme;
  a receive beamformer including a receive signal processing unit configured to process the echo signals received in response to one transmit beam to produce a plurality of receive lines of echo signals at the laterally spaced line positions within the width or the aperture of each of the transmit beams of the said plurality of transmit beams;
  a focalization delay and phase equalization delay module which applies to each receive signal contribution of each channel or transducer element the corresponding focalization and phase shift equalization delays for re-aligning the time of arrival of the receive signal contributions at the transducer elements of the transducer array from each reflecting or focus point and for equalizing the phase shift variance among receive line signals for each reflecting or focus point at a common line position, the said receive line signals resulting from transmit beams of different transmit beam positions based on stored delay and phase shift values among receive lines at a common line;
  a summer for summing for each receive line at each receive line position within the width or aperture of a transmit beam the re-aligned and phase shift equalized receive signal contributions of the transducer elements from focus points on the said receive line position after having applied to them the focalization delays and the phase shift equalization delays;
  a memory connected to the receive beamformer and configured to store the said plurality of processed received lines of echo signals along a common receive line position resulting from transmit beams of different transmit beam positions;
  a line combination module connected to the said memory and configured to combine echo signals of receive lines from different transmit beams which are spatially related to a common line position to produce line image data;
  an image generation unit producing an image using the said line image data.

In accordance with a further embodiment an apodization module is provided applying anodization weights to the receive signals.

In accordance with embodiments, the system further comprises a pre-calculated table, stored in a memory. The pre-calculated table comprises real times of arrival of the receive signals relative to a predetermined reflection point. In accordance with embodiments, the system further comprises a processor configured to calculate real times of arrival of the receive signals relative to a predetermined reflection point. In accordance with embodiments, the processor is configured to calculate the focalization delay for each receive signal and the phase shift among receive lines at a common line position resulting from transmit beams of different transmit beam positions and to add the focalization delays of each of the receive signals relative to a predetermined reflection point with the corresponding phase shift and apply the result of the said summation as a combined delay parameter to the said received signals.

In accordance with embodiments, the memory is configured to store program instructions and the circuit includes a processor that, when executing the program instructions, is configured to apply combined delay resulting from the sum of focalization delays and phase shifts to the receive signals. Optionally, the system further comprises a processor configured to provide parallel multi-line receive (PMR) beamforming in connection with individual view lines acquired in parallel contemporaneously with a focusing function.

According to an embodiment herein the beamformer is a multiline beamformer comprising a multiline processor for each receive line encompassed by the aperture or the width of each transmit beam centered on a certain transmit line position.

According to an embodiment each multiline processor comprises a number of channels corresponding to the number of probe channels or transducer elements.

According to a further embodiment the ultrasound system is further provided with a motion detector generating a parametric value representing the level of motion and cooperating with a ultrasound beam width or aperture controller which varies the width or the aperture of the transmit beam relatively to the level of motion.

According to an embodiment, input means are provided for setting a motion level threshold and a comparator compares the values of the parameter representing the level of motion determined by the motion detector unit with the threshold, causing the width of the ultrasound beam to be modified as a function of the determined value of the level of motion in relation to the said threshold.

According to an embodiment the ultrasound beam width or aperture controller may operate automatically triggered by the motion detector unit.

In a variant embodiment which can be alternative to or combined with the above embodiment providing automatic operation of the ultrasound beam width or aperture controller, the said ultrasound beam width or aperture controller may be provided with manual input organs for controlling the operation of the ultrasound beam width or aperture controller. In a variant embodiment, a display may be provided in combination indicating the threshold value set for the parameter representing the level of motion and the setting selected by the manual input organs and/or determined by the automatic operation mode of the said beam width or aperture controller. In a variant embodiment the display may also indicate the number of lines encompassed by the ultrasound beam either with an alphanumerical indication and/or with a pictogram showing a transmit beam aperture and the lines encompassed by the said aperture.

According to a further embodiment which can be provided as an alternative or in combination with the above embodiments, an imaging mode selector may be provided for switching the imaging mode of the ultrasound system from a so-called B-mode imaging or a so called Doppler imaging. This selector may communicate the selected imaging mode to the ultrasound beam width or aperture controller and the controller operates in varying the width or the aperture of the beam in a predetermined way as a function of the selected imaging mode. Also in this case the width or aperture variation may be carried automatically or by means of a manual input organ controlling the beam width or aperture controller.

According to an embodiment, the ultrasound motion detector and/or the beam width or aperture controller may be in the form of dedicated hardware or at least partially in the form of a program coding the instruction for configuring a processor and peripherals thereof in such a way as to carry out the functions of the motion detector and of the beam width or aperture controller.

If a GUI is provided also the organs for manual input of the beam width or apertures may consist in a program coding the instructions for configuring a processor such as a graphic processor to print on a screen the images of manual input organs and/or the threshold values for the level of motion, the values of the width of the beam and other data related to the above described functions of varying the beam width.

In a further embodiment of the ultrasound system a transmit beam line spacing controller is provided which is manually or automatically driven to modify the spacing between transmit beam line positions encompassed by the transmit beam aperture as a function of a detected motion.

According to still a further embodiment which can be provided alternatively or in combination, the system may be provided also with a receive beam line spacing controller which varied the receive beam line positions encompassed by the beam aperture as a function of motion detection.

Also in this case the spacing may be varied by manually or automatically.

Both the above variant embodiments, the line spacing controller may be provided with manual input organs for controlling the operation distance between laterally adjacent lines. In a variant embodiment, a display may be provided in combination indicating the threshold value set for the parameter representing the level of motion and the setting selected by the manual input organs and/or determined by the automatic operation mode of the said line spacing controllers. In a variant embodiment the display may also indicate the number of lines encompassed by the ultrasound beam either with an alphanumerical indication and/or with a pictogram showing a transmit beam aperture and the lines encompassed by the said aperture.

According to a further embodiment which can be provided as an alternative or in combination with the above embodiments, an imaging mode selector may be provided for switching the imaging mode of the ultrasound system from a so-called B-mode imaging or a so called Doppler imaging. This selector may communicate the selected imaging mode to one or both the line spacing controllers and the controller operates in varying the distance between transmit or receive lines in a predetermined way as a function of the selected imaging mode. Also in this case the width or aperture variation may be carried automatically or by means of a manual input organ controlling one or both the line spacing controllers, respectively for the transmit beams and of the receive beams.

According to an embodiment, the ultrasound motion detector and/or the spacing controllers may be in the form of dedicated hardware or at least partially in the form of a program coding the instruction for configuring a processor and peripherals thereof in such a way as to carry out the functions of the motion detector and of the controllers.

If a GUI is provided also the organs for manual input of the spacing of the transmit beam line and/or of the receive beam lines may consist in a program coding the instructions for configuring a processor such as a graphic processor to print on a screen the images of manual input organs and/or the threshold values for the level of motion, the values of the transmit beam line spacing and/or of the receive beam line spacing and other data related to the above described functions.

Embodiments herein relate to a retrospective dynamic transmit focusing beamforming method for ultrasound signals by means of an ultrasound machine acquiring diagnostic images which ultrasound machine comprises an array of electroacoustic transducers arranged according to a predetermined arrangement and with predetermined relative positions from each other and which transducers are used, alternatively, for generating an excitation ultrasound wave and for receiving the reflection echoes (target) from the tissues under examination. Said reflection echoes generate electric signals corresponding to the received acoustic wave which electric signals are processed by each processing channel and are combined with each other to reconstruct an electric signal that corresponds to the combination of the contributions of the reflection signal of each transducer deriving from a certain reflection target or point, which method comprising the following steps:
a) transmitting a plurality of transmit beams from an array transducer, each transmit beam being centered at a different position along the array and each transmit beam having a width or an aperture encompassing a plurality of laterally spaced line positions, each transmit beam width or aperture overlapping at least partially at least the width or the aperture of the immediately adjacent transmit beam or of more laterally spaced transmit beams;
subjecting the receive signal of each transducer to an analog/digital conversion;
b) receiving echo signals with the array transducer;
c) processing the echo signals received in response to one transmit beam to produce a plurality of receive lines of echo signals at the laterally spaced line positions within the width or the aperture of the transmit beam;
d) repeating the receiving step b) and the processing step c) for the additional transmit beams of the plurality of transmitted transmit beams of step a);
e) equalizing the phase shift variance among receive lines at a common line position resulting from transmit beams of different transmit beam positions;
f) combining echo signals of receive lines from different transmit beams which are spatially related to a common line position to produce image data; and
g) producing an image using the image data;
and in which the step e) of equalizing the phase shift is carried out concurrently with in the processing step c) and d).

Embodiments herein provide improvements to the method allowing the process to be simplified, while keeping the focusing accuracy high and while reducing the computational burden without the need for a specific particular hardware structure.

A further aim of the at least some embodiments herein is to improve the method such to allow delays and phase correction coefficients to be put in table on the basis of general geometrical characteristics of the ultrasound system and particularly of the transducer array.

Still another aim, in accordance with at least some embodiments, is to provide a beamforming processor that allows the method according to the embodiments herein to be carried out.

A further aim is to provide an ultrasound system for acquiring diagnostic images that comprises said beamforming processor.

Embodiments herein achieve the above aims by methods according to what is described above wherein the phase shift correction between received echo signals from a reflecting point on a common receive line position generated by a plurality or a certain number of transmit beams having an aperture or width containing the said receive line position in order to carry out the equalization of the said receive signals is added to the focalization delays to be applied to the receive signal contribution of each transducer of the transducer array and applied to the said contribution as a combined delay correction.

Advantageously for the signal contribution of each channel a further weight is applied, the said weight is applied to the combined or summed equalized contributions of each channel for each reflection point on a common receive line position.

In order to determine the image data along a certain line position the receive line signals for a common receive line position are obtained from the multiline beamformer for each or for some of the receive line position encompassed by at least a number of transmit beams of the said plurality of transmit beams. After having beamformed the receive signals for each of the said receive lines by applying contemporaneously the focalization delays and the phase equalization delays to the receive signal contributions of each or of some selected transducer elements of the transducer array, the said receive lines are stored and combined together coherently.

Further characteristics and improvements of the embodiments herein are the subject matter of the sub-claims.

Embodiments herein relate also to a beamforming processor for carrying out the method described above which beamforming processor comprises:
a plurality of multiline processors each one for one of the receive lines encompassed by the aperture or the width of each transmit beam centered on a certain transmit line position;
each multiline processor comprising a plurality of processing channels each one for processing the receive signal of a corresponding transducer element of a transducer array;
an analog-digital converter for converting the receive signals of each channel;
each multiline processor comprising a unit for determining and applying the focalization delays and the phase shift corrections with respect to the signal components of the individual channels;
the unit for determining the focalization delays and the phase shift corrections comprises:
a calculation unit or a pre-calculated table of the real times of arrival of the receive signal components deriving from a predetermined reflection point on a certain receive line corresponding to the multiline processor;
means for calculating the phase shift of the receive line contributions deriving from a reflection point on the said certain receive line corresponding to the multiline processor and from a certain number of transmit beams of the plurality of transmit beams which aperture or width encompasses the position of the said reflection point;
means for summing the said focalization data and the said phase shift data for each channel;
an adder for adding the contribution of the said channels;
a memory configured to store the receive line signals generated by each multiline processor;
an adder for combining together a certain number of receive line data stored in the memory and which receive line data is processed by at least a part of the multiline processors and is relative to a common line position or the said receive line data.

According to a further embodiment each multiline processor is provided with a unit applying an apodization weight to the receive signals of each channel of the multiline processor after applying said combined delay and phase shift correction to the said channels and before adding together the corrected contributions of each channel.

Still to another embodiment herein provides for a unit for applying a RTB weight to the receive signals resulting from summation of the contributions of the channels of a multiline processor before storing the said signal in the memory for the image data lines.

According to an embodiment, the retrospective transmit beam focusing may be applied to the RF data directly acquired by the system or to transformed data according to different transformations as for example as a phase/quadrature (I/Q) transformation, or similar.

BRIEF DESCRIPTION OF THE DRAWINGS

Further improvements and characteristics of the embodiments herein will be clear from the following description of some non-limiting embodiments schematically shown in the annexed figures wherein:

FIG. 3A illustrates diagrammatically the relation between the echo signals reflected from a common reflection point on a common receive line which echo signals are generated by transmit beams focused on centerlines having different positions and on whose aperture is such that each transmit beam encompasses the said reflection point or receive line.

DETAILED DESCRIPTION

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Figure 1A:
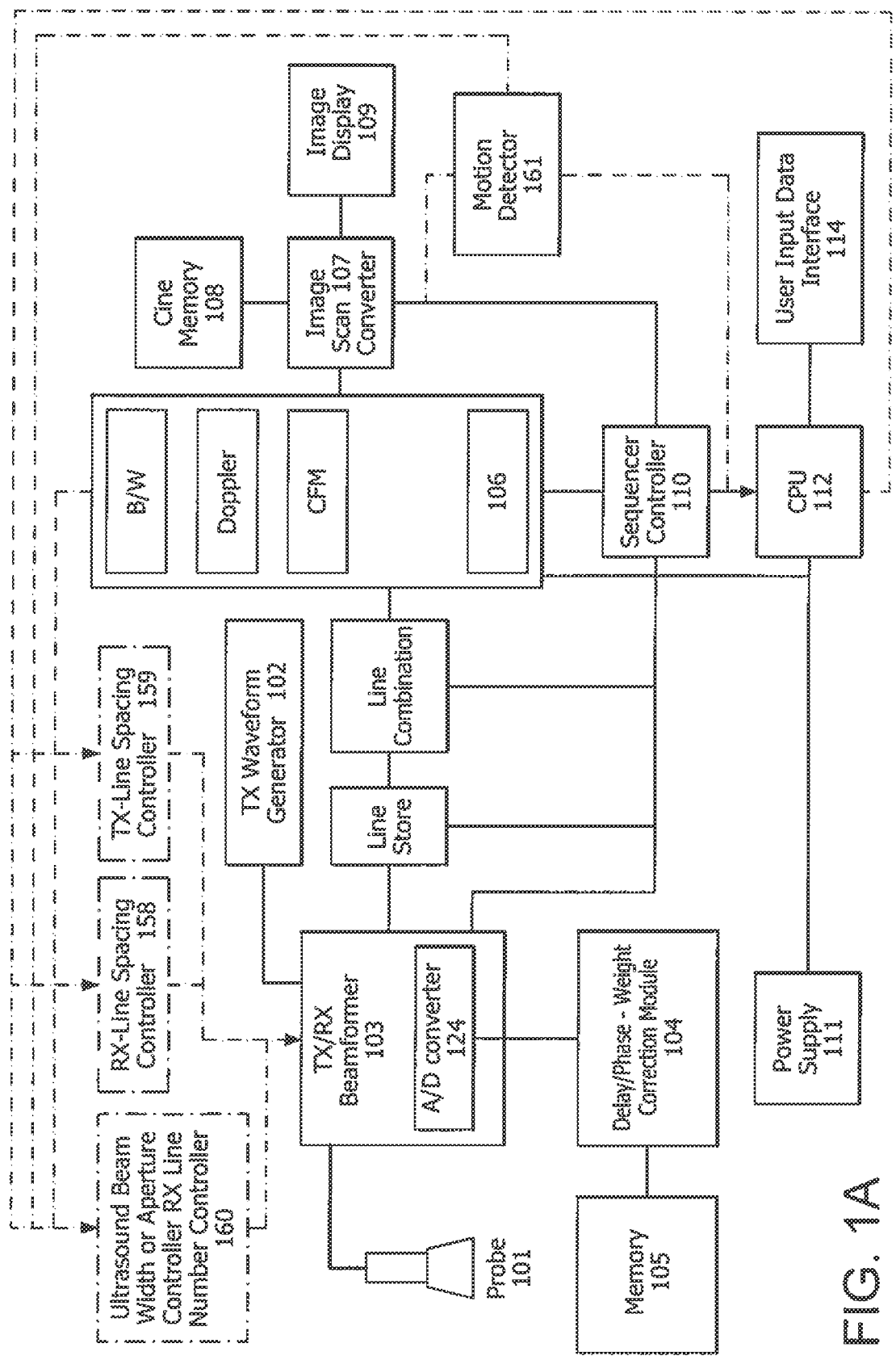
FIG. 1A illustrates a block diagram of an ultrasound system according to an embodiment.

FIG. 1A illustrates a high-level block diagram of an ultrasound system implemented in accordance with embodiments herein. Portions of the system (as defined by various functional blocks) may be implemented with dedicated hardware, analog and/or digital circuitry, and/or one or more processors operating program instructions stored in memory. Additionally, or alternatively, all or portions of the system may be implemented utilizing digital components, digital signal processors (DSPs) and/or field programmable gate arrays (FPGAs) and the like. The blocks/modules illustrated in FIG. 1 can be implemented with dedicated hardware (DPSs, FPGAs, memories) and/or in software with one or more processors.

The ultrasound system of FIG. 1 includes one or more ultrasound probes 101. The probe 101 may include various transducer array configurations, such as a one dimensional array, a two dimensional array, a linear array, a convex array and the like. The transducers of the array may be managed to operate as a 1D array, 1.25D array, 1.5D array, 1.75D array, 2D array, 3D array, 4D array, etc.

The ultrasound probe 101 is coupled over a wired or wireless link to a beamformer 103. The beamformer 103 includes a transmit (TX) beamformer and a receive (RX) beamformer that are jointly represented by TX/RX beamformer 103. The TX and RX portions of the beamformer may be implemented together or separately. The beamformer 103 supplies transmit signals to the probe 101 and performs beamforming of "echo" receive signals that are received by the probe 101.

A TX waveform generator 102 is coupled to the beamformer 103 and generates the transmit signals that are supplied from the beamformer 103 to the probe 101. The transmit signals may represent various types of ultrasound TX signals such as used in connection with B-mode imaging, Doppler imaging, color Doppler imaging, pulse-inversion transmit techniques, contrast-based imaging, M-mode imaging and the like. Additionally, or alternatively, the transmit signals may include single or multi-line transmit, shear wave transmit signals and the like.

The beamformer 103 performs beamforming of the transmit beams in order to focalize the transmit beams progressively along different adjacent lines of sight covering the entire ROI. The beamformer performs also beamforming upon received echo signals to form beamformed echo signals in connection to pixel locations distributed across the region of interest. For example, in accordance with certain embodiments, the transducer elements generate raw analog receive signals that are supplied to the beamformer. The beamformer adjusts the delays to focus the receive signal along one or more select receive beams and at one or more select depths within the region of interest (ROI). The beamformer adjusts the weighting of the receive signals to obtain a desired apodization and profile. The beamformer applies weights and delays to the receive signals from individual corresponding transducers of the probe. The delayed, weighted receive signals are then summed to form a coherent receive signals.

The beamformer 103 includes (or is coupled to) an A/D converter 124 that digitizes the receive signals at a selected sampling rate. The digitization process may be performed before or after the summing operation that produces the coherent receive signals.

Optionally, a dedicated sequencer/timing controller 110 may be programmed to manage acquisition timing which can be generalized as a sequence of firings aimed at select reflection points/targets in the ROI. The sequence controller 110 manages operation of the TX/RX beamformer 103 in connection with transmitting ultrasound beams and measuring image pixels at individual LOS locations along the lines of sight. The sequence controller 110 also manages collection of receive signals.

One or more processors 106 perform various processing operations as described herein.

In accordance with embodiments herein the beamformer 103 includes an output that is configured to be coupled to an ultrasound probe 101 and sends signals to the transducer elements of the probe 101.

According to an embodiment herein the sequencer 110 controls the beamformer in order to generate and transmit a plurality of transmit beams which are focalized in such a way as to show an aperture or a beam width encompassing a certain number of line of sights ore of receive lines. The transmit beams of the said plurality being progressively laterally shifted along the array of transducer elements of the probe and thus along the ROI for scanning the entire ROI. A certain line of sight or a certain receive line will be encompassed by a certain number of different transmit beam of the said plurality as long as the said line of sight position or the said receive line position falls within the aperture of the said transmit beams or within the width of the said transmit beams. Thus for a reflecting point on a certain receive line or line of sight having a certain line position within the ROI and relatively to the transducer array of the probe a certain number of receive signals contributions are received each one deriving from a different transmit beam whose center transmit line having different lateral shifts relatively to the said reflecting point and to the corresponding receive line.

The receive data relatively to the echoes from the said reflecting point is a combination of the contributions of the receive signals from the said reflecting point deriving from the said certain number of transmit beams.

In accordance with embodiments herein, the beamformer 103 includes an input that is configured to be coupled to an ultrasound probe 101 and receive signals from transducers of the ultrasound probe 101. The memory 105 stores time delays to align contributions of reflection signals received by the transducers of the array of the probe 101 from the reflectors in the ROI. The memory 105 also stores phase corrections to correct phase differences of the receive signals contributions for each transducer element and deriving from each of the said certain number of differently laterally shifted transmit beams relatively to the receive line or line of sight on which the said reflector point is located.

A delay/phase correction (DPC) module 104 is coupled to the memory 105 and provides various delays and corrections to the beamformer 103. For example, the DPC module 104 directs the beamformer 103 to apply time delay and phase correction to the receive signals to form delayed receive signals. The beamformer 103 then sums, in a coherent manner, the delayed receive signals to obtain a coherent receive signal in connection with a reflection point or a reflection target.

Optionally, the memory 105 may store a common phase shift correction in connection with multiple channels. Different phase shift corrections may be stored in connection with various corresponding channels in the case of multiple receive signals are received along a common receive line position but due to a certain number of different transmit beams each one having a laterally shifted transmit center line and an aperture or width encompassing the receive line position. The memory 105 may also store weights such as apodization weights and/or RTB weights.

As explained herein, the beamformer 103 (circuitry) is configured to apply contemporaneously to each receive signal contribution of each transducer element from a reflection point a beamforming focalization delay and a phase shift equalization delay so called RTB delay. The said beamforming focalization delay being calculated basing on the time of arrival of the said signal contribution to a transducer element when traveling from the reflection point to the said transducer element and the said phase shift equalization delay being determined according to the difference in phase of the wave front reaching the reflecting point relatively to the phase of the wave fronts reaching the same reflecting point and being of further transmitted beams which are laterally shifted each other.

Optionally, the memory 105 may store a pre-calculated table, where the pre-calculated table comprises real times of arrival of the receive signals relative to a predetermined reflection point. Optionally, the processor 106 may be configured to calculate real times of arrival of the receive signals relative to a predetermined reflection point. Optionally the memory 105 may store a pre-calculated table, where the pre-calculated table comprises pre-calculated phase shift equalization delays to be applied contemporaneously to the beamforming focalization delays to the receive signals of a receive line along a certain line of sight or a certain receive line position deriving from a certain number of transmit beams being differently laterally shifted relatively to the said receive line position, the number of the said transmit beams being set by setting a certain aperture or lateral width of the said transmit beams. Optionally the memory 105 may store a pre-calculated table of the said phase shift equalization delays which are pre-calculated for one or more of different transmit beams apertures or widths.

Optionally, the processor 106 may be configured to calculate the said phase shift equalization delays for one or more of different transmit beams apertures or widths.

Optionally, the beamformer 103 circuitry may further comprise an adder unit for adding the beamforming delays and the phase shift equalization delays (RTB delays) for the receive signal contributions deriving from each reflecting point.

In accordance with certain embodiments, at least a portion of the beamforming process may be implemented by the processor 106 (e.g., in connection with software RTB beamforming). For example, the memory 105 may store beamforming related program instructions that are implemented by the processor 106 to contemporaneously apply beamforming delays and phase shift equalization delays to the receive signals.

The processor 106 and/or CPU 112 also performs conventional ultrasound operations. For example, the processor 106 executes a B/W module to generate B-mode images. The processor 106 and/or CPU 112 executes a Doppler module to generate Doppler images. The processor executes a Color flow module (CFM) to generate color flow images. The processor 106 and/or CPU 112 may implement additional ultrasound imaging and measurement operations. Optionally, the processor 106 and/or CPU 112 may filter the first and second displacements to eliminate movement-related artifacts.

An image scan converter 107 performs scan conversion on the image pixels to convert the format of the image pixels from the coordinate system of the ultrasound acquisition signal path (e.g., the beamformer, etc.) and the coordinate system of the display. For example, the scan converter 107 may convert the image pixels from polar coordinates to Cartesian coordinates for image frames.

A cine memory 108 stores a collection of image frames over time. The image frames may be stored formatted in polar coordinates, Cartesian coordinates or another coordinate system.

An image display 109 displays various ultrasound information, such as the image frames and information measured in accordance with embodiments herein. The display 109 displays the ultrasound image with the region of interest shown.

A control CPU module 112 is configured to perform various tasks such as implementing the user/interface and overall system configuration/control. In case of fully software implementation of the ultrasound signal path, the processing node usually hosts also the functions of the control CPU.

A power supply circuit 111 is provided to supply power to the various circuitry, modules, processors, memory components, and the like. The power supply 111 may be an A.C. power source and/or a battery power source (e.g., in connection with portable operation).

Figure 1B:
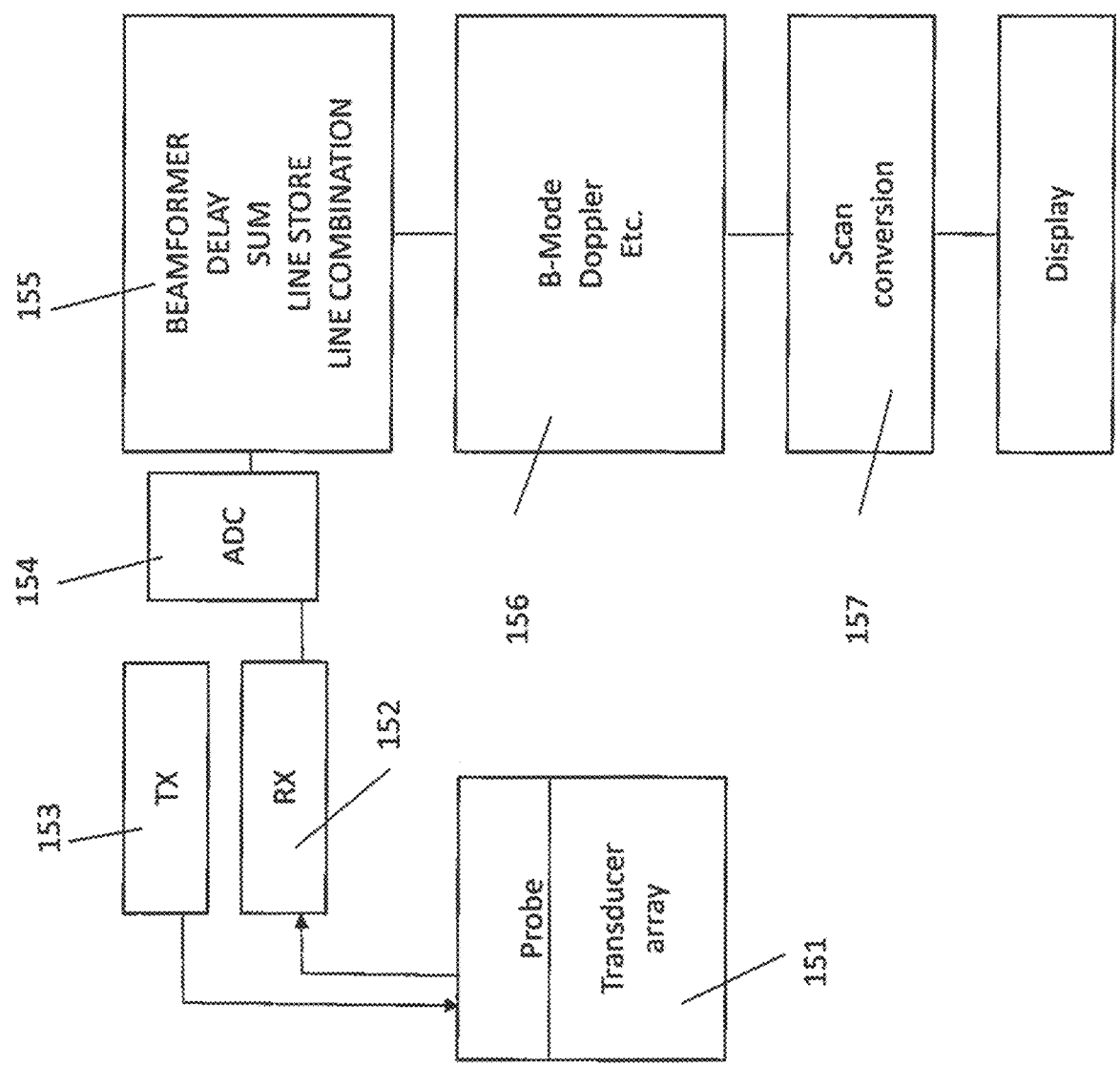
FIG. 1B illustrates a block diagram of an ultrasound system according to an embodiment.
Figure 2:
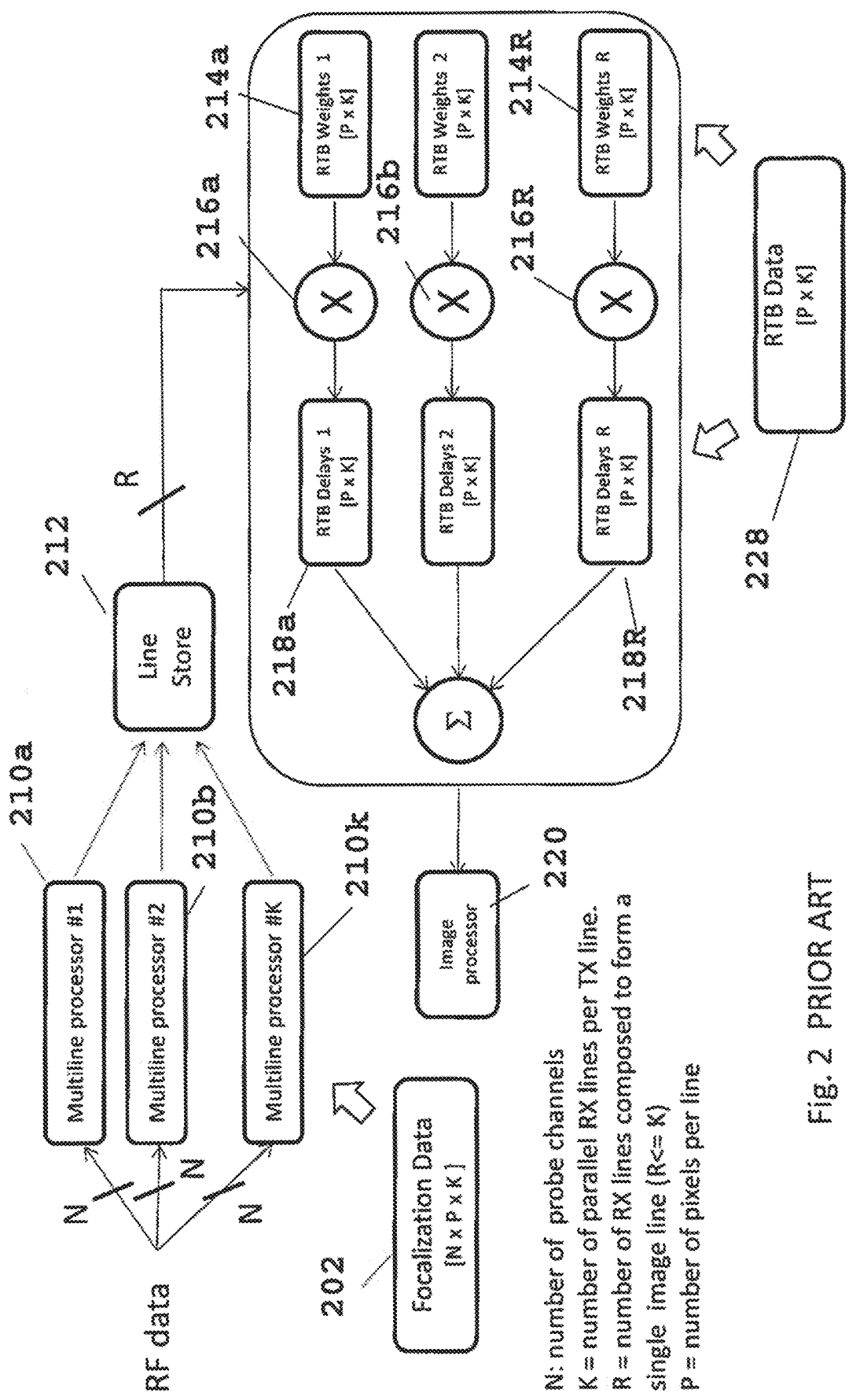
FIG. 2 illustrates a block diagram of an ultrasound system according to the prior art.

FIG. 1B illustrates a high-level block diagram of an ultrasound system implemented in accordance with embodiments herein. The ultrasound machine for acquiring diagnostic images comprises a probe 151 provided with an array of electroacoustic transducers intended to transform excitation electric signals sent thereto into ultrasound acoustic signals and vice versa the received acoustic signals into corresponding electric signals.

A transmit section and a receive section 152, 153 are connected alternatively one another with the probe to provide to each individual transducer an excitation signal of the corresponding ultrasound pulse and to receive the electric signal corresponding to an acoustic pulse that has hit the transducer.

The receive signals of the transducers are each one sent in an independent manner through a dedicated channel or by a multiplexer to an analog digital converter 154 that samples said signals with a predetermined sampling rate and it provides output digitized receive signals of each transducer/channel.

Therefore, digitized signals are subjected to a processing by a so called beamforming processor 155 that carries out the time alignment of the contributions of the receive signal of each channel correspondingly to the travel time of the signal reflected by a predetermined reflection point from said reflection point to the corresponding transducer.

Since the individual transducers of the array provided on the probe have positions different from each other, they necessarily have different distances from the reflection point and therefore the echo signal deriving from such point reaches each individual reflector in a different moment.

The focusing process performs the time re-alignment of the contributions of the receive signal of each transducer deriving from the same reflection point and therefore to sum together such contributions in a coherent manner.

The process is repeated for each datum along each line forming a two-dimensional or three-dimensional image.

In the beamforming process, the receive signals are subjected to time re-alignment and phase shift equalization.

The signals obtained by the coherent sum of the time re-aligned contributions of the individual transducers and by the coherent combination of the receive signal contributions along a receive line position or line of sight due to differently laterally shifted transmit beams encompassing the said receive line position or line of sight are provided to a processing section 156 for generating images according to different modes such as B mode, Doppler, color Doppler, etc. that then are transmitted to a scan converter 157 in order to be displayed, printed, stored or subjected to other image processing.

Figure 4:
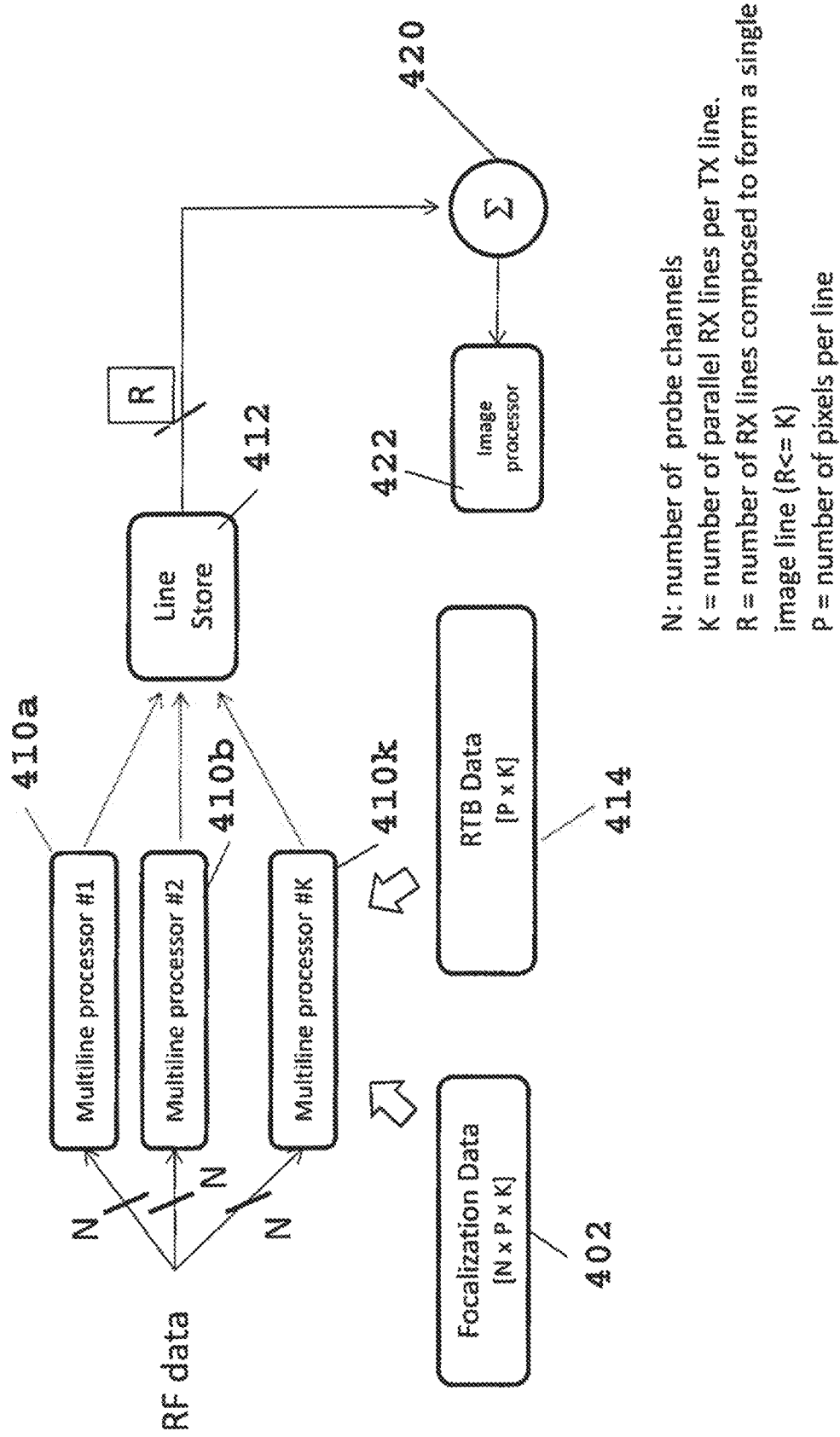
FIG. 4 illustrates a block diagram of the retrospective beamforming method according to an embodiment.
Figure 5:
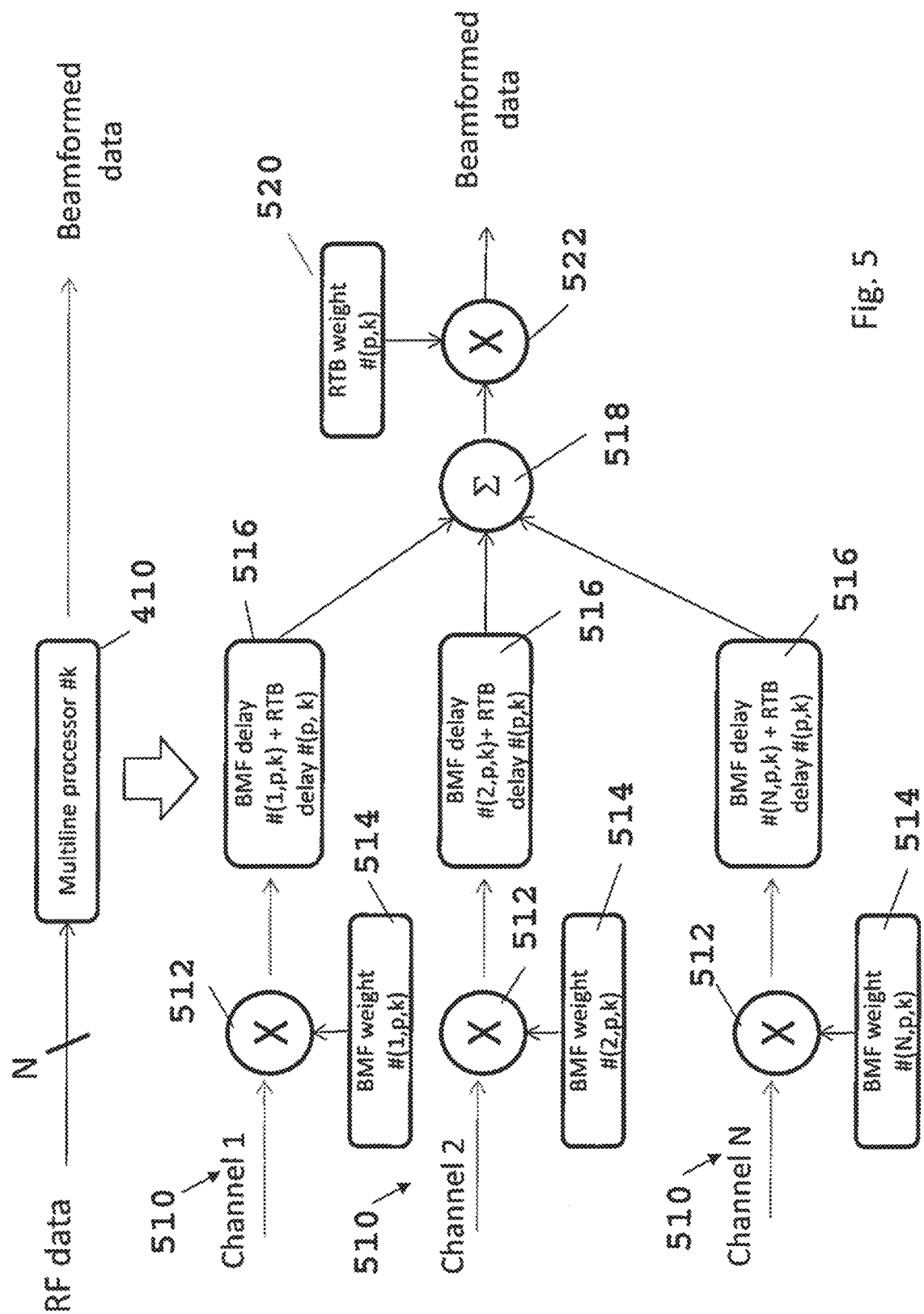
FIG. 5 illustrates a block diagram of the architecture of each multiline processors of the beamformer according to embodiments herein.

With reference to FIGS. 4 and 5 they show the block diagrams of an embodiment of a multiline beamforming processor according to the embodiments herein.

A transducer array comprising a number N of transducer elements of an ultrasound probe is driven by a transmit beamformer in such a way that selected groups of the transducer elements are actuated at respectively delayed times to transmit beams focused at different focal regions along the array. The number of the selected transducer elements may be equal or optionally and preferably smaller than the total number of transducer elements of the array of transducer elements. Different number of transducer elements may be selected for the transmit beam generation and for the receipt of the echoes signals generated by the said transmit beam.

The echoes received by each transducer element of the array in response to each transmit beam are applied to the inputs of a multiline beamformer comprising a number K of multiline processors 410a-410k. The said number K corresponding to the number of receive lines falling within the aperture or width of each transmit beam.

Each multiline processor 410a-410k processes the k parallel receive lines RX encompassed by every transmit beam TX. Each multiline processor applies contemporaneously focalization beamforming delays 402 and phase shift equalization delays 414 to the receive signal and if desired, apodization weights to weight the received echoes from the array elements.

The focalization beamforming delays are applied to the receive signal contributions of each transducer element of the array in order to re-align the said receive signal contribution in relation to the relative position of each transducer element and each reflection point on a certain receive line or a certain line of sight.

In a RTB beamforming system the phase shift equalization delays are applied to the received signals of each reflecting point on a certain receive line of on a certain line of sight in order to coherently re-align the phases of the receive signals along a certain receive line position deriving each from a transmit beam having different lateral shifts relating to the said receive line position of the said line of sight.

As it appears clearly for each of the k-receive lines encompassed by a transmit beam width the phase shift equalization data are different and thus each of the multiline processors 410a-410k are differentiate one from the other by the said RTB delays (i.e. the said phase shift equalization delays) which apply for the receiving line K processed by the corresponding multiline processor.

The RTB delays are used to equalize the phase shift variance that exists from line to line for the multilines with differing transmit-receive beam location combinations, so that signal cancellation will not be caused by phase differences of the combined signals. Due to the fixed geometry of the Rx and TX paths and of the lateral shift steps of the transmit aperture in relation to the geometry of the transducer array the delays can be calculated in real time or even calculated in advance and stored in a memory, for example in the form of a table.

The outputs of the multiline processors 410a-410k are coupled to a line memory 412 which stores the received multilines until all of the R multilines needed to form a line of display data have been acquired. The group of receive lines R along a common receive line position are used to form a particular line of display data and the number R of the receive lines is equal or less than the number of receive lines K falling within the width of a transmit beam TX.

The R receive lines are combined in a summer 420.

The combined signal by the summer 420 is fed to an image processor 422, which converts the coherently summed receive signals in image data along a corresponding line of sight and in a displayable image according to one or more of the previously described processing units and methods.

FIG. 5 shows the architecture of a multiline processor of the multiline beamformer according to an embodiment, identical functional blocks or having identical functions as in FIG. 4 have the same reference numbers.

The receive signals of the N transducer elements are fed to N-dedicated processing channels 510 of a multiline processor 410. A multiplier 512 applies to the receive signals of each channel a BMF weight which considers for example apodization and/or the position of the corresponding transducer element relatively to the receive line. The said BMF-weight being stored in a memory 514 as a pre-calculated value or as a value calculated by a processor unit.

Each channel of the multiline processors 510 is provided with a circuitry 516 for applying a beamforming delay and a RTB delay i.e. a phase shift equalization delay.

According to an embodiment herein the beamforming or focalization delays are calculated considering the different time of arrival of the echoes from a reflection point. The delays applied to such signal contribution of each transducer element and thus of each channel carry out the time alignment of the contributions of the receive signal of each channel correspondingly to the travel time of the signal reflected by a predetermined reflection point from said reflection point to the corresponding transducer element. Since the individual transducers of the array provided on the probe have positions different from each other, they necessarily have different distances from the reflection point and therefore the echo signal deriving from such point reaches each individual reflector in a different moment.

According to a more general embodiment, the focalization data may be computed separately for each transducer array and for each focus point of each of the receive line positions. Similarly, the phase shift equalization delays has to be determined separately for each focus point on each receive line position encompassed by the transmit beam aperture.

This more general case applies also to the focalization weights 514 of FIG. 5.

This more general case finds application in combination with phased array or virtual convex probes which do not allow to define a common rule for determining the focusing delays the phase shift equalization delays and the apodization weights.

Figure 10:
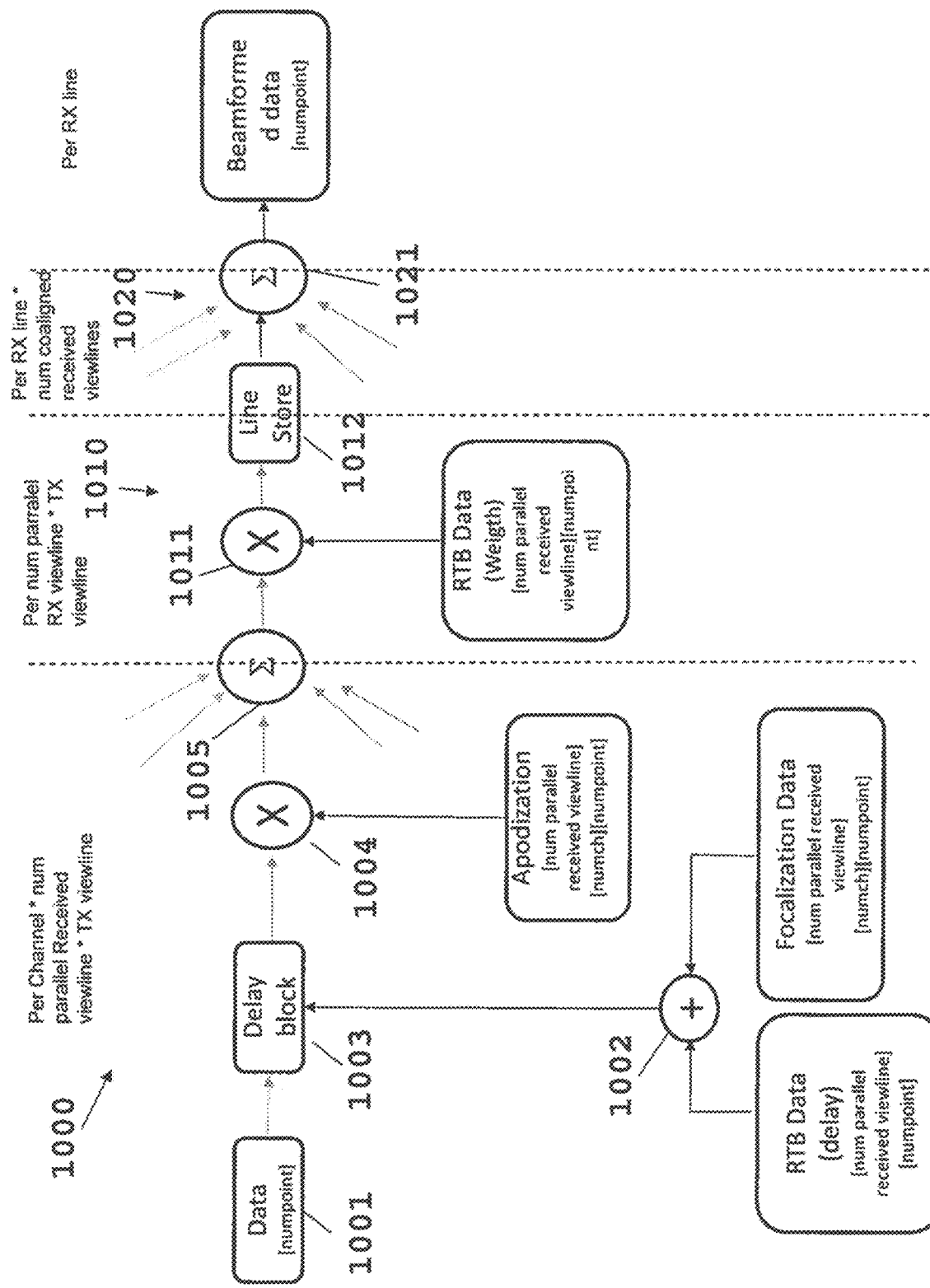
FIG. 10 is a diagram describing the steps of the method according to an embodiment.

The above is clearly expressed in the FIGS. 4, 5 and 10 where the weights and the focusing delays (Focalization Data) are indicated as a function of the parameters N: number of probe channels; K=number of parallel RX lines per TX line and P=number of pixels per line.

The phase shift equalization delays (RTB Data) and the phase shift equalization weights (RTB weights) are expressed as a function of K=number of parallel RX lines per TX line and P=number of pixels per line.

Considering other kind of probes, a fixed rule may be defined allowing to more easily generate the pre-calculated tables of delay or weight values and even direct and real time calculation of the delay values.

In this particular case the focalization delays (BMF delay) and the focalization weights (BMF weight) are calculated as a function of the channel N and of the pixel per line P, whereas RTB delays and RTB weights are calculated, as in the general case, as a function of receive line K and pixel per line P. It has to be noted that since the pitch between adjacent transducer elements along the one dimensional or bi-dimensional array of transducer is identical for every transducer element of the said array, the beamforming or focalization delays realigning the signal contribution processed by each one of the channels are identical for every multiline processor, while the RTB delay for equalizing the phase shift between the receive signals along the same line position or line of sight which are due to differently laterally shifted transmit beams are different for every one of the multichannel processors 510 each one dedicated to processing the multiline signals along a certain receive line position or line of sight.

According to one embodiment the RTB delays may be pre-calculated for a certain transmit beam aperture or width and thus for a certain number of receive line positions which fall within the said certain width or aperture of the transmit beams. Optionally RTB delays can be pre-calculated for a set of different transmit beams width or apertures so that image data acquisition can be carried out by selecting a certain transmit beam aperture or width. Optionally RTB delays may be pre-calculated also in combination with different measures of the lateral shift step. The said circuitry 516 for applying the Beamforming delays and the RTB delays to each signal processed by each channel may comprise a memory configured to store the RTB delays according to one or more of the above variants. Optionally the said RTB delays may be pre-calculated by an external processor unit or by a processor unit associated or comprised in the said circuitry 516.

The signal contributions of each channel 510 to which the apodization weights has been applied and to witch the beamforming delay related to the corresponding channel and the RTB delay related to the receive line position to which a corresponding multiline processor 410 is associated are fed to a summer 518 which adds together the signal contributions of the channels 510 having bean realigned in relation of their time of arrival by the beamforming delays and being subjected to a phase shift equalization which provides for compensating the phase shift between the receive signals along a common receive line position or line of sight which are due to the fact that the said receive signals are generated by the echoes from reflectors on the common receive line position but deriving from different transmit beams each one being shifted in a different measure from the said receive line position i.e. having a different lateral distance from the said receive line position.

In one embodiment shown in FIG. 5 the summed, realigned and phase equalized receive signal contribution of each channel may be subjected by a further weighting by a RTB weight.

The said RTB weight modulates the relevance of the receive signals processed by each of the multiline processors 410 in relation to the position of the receive line position associated to the multiline processor 510 relatively to the transmit beam or to the position of the reflecting point.

In embodiment herein the RTB weight which is different for every multiline processor 410 may be stored in memory 520 and may be applied to the receive signal provided by the adder 518.

According to an embodiment the multiline processors comprise each a multiplier 522 for applying the said RTB weights to the said signal processed by the adder 518.

According to the embodiment of FIG. 4, the beamformed data along a receive line position processed by each multi-line processor 410a to 410k are stored in a memory 412. The receive signals along a certain receive line are then coherently summed. The number of coherently summed receive lines can be chosen and can be maximally equal to the number of receive lines encompassed by each transmit beam.

The coherently summed multiline contributions along a certain line of sight or a certain receive line position are fed to an image processing unit which converts the beamformed data in displayable image data and which can be configured according to one or more of the embodiments described herein according to known image processing techniques applied in ultrasound imaging.

Figure 6:
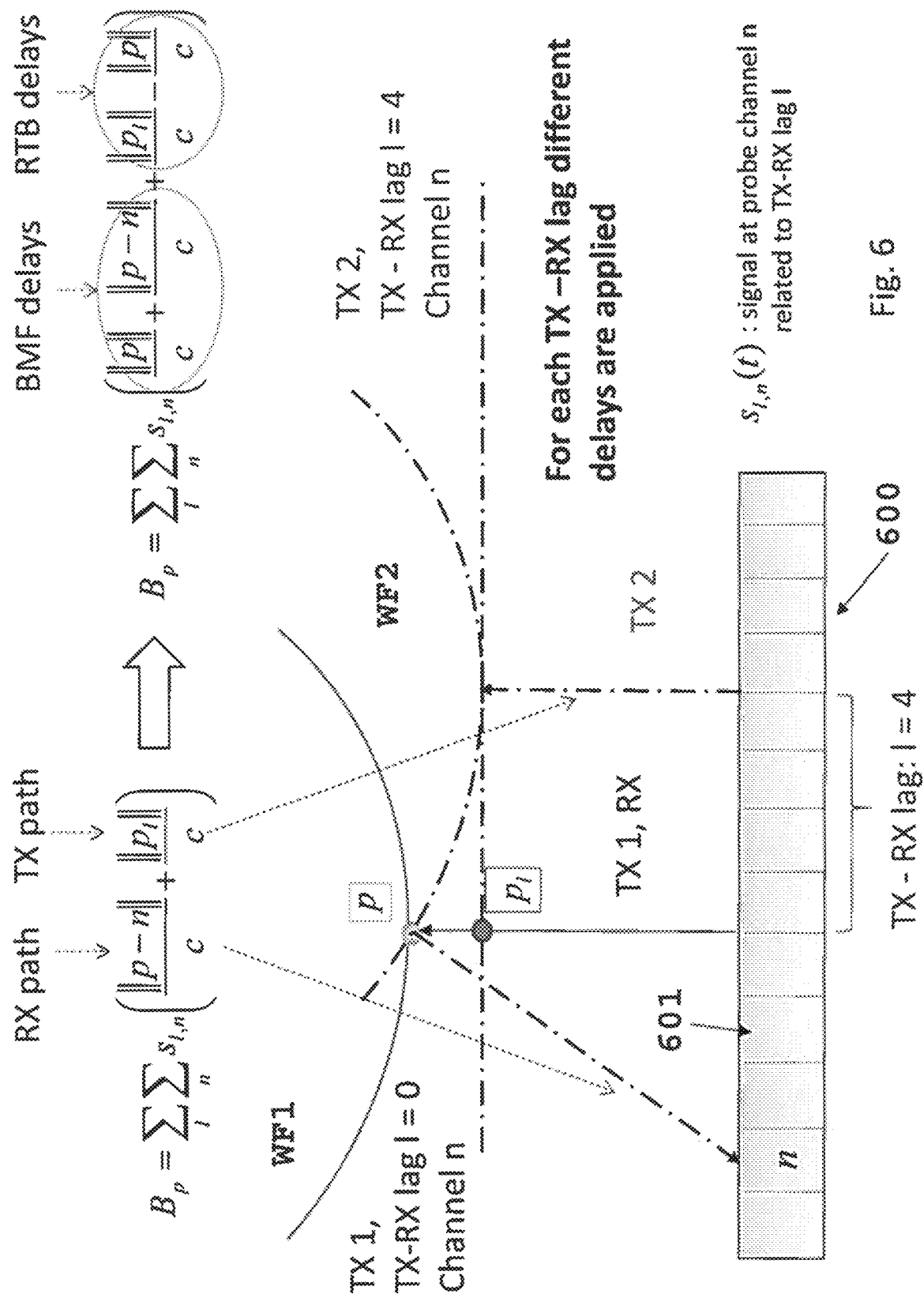
FIG. 6 illustrates with a diagram according to FIGS. 3A and 3B the effect of the delay and phase shift correction applied by the method for carrying out retrospective transmit beamforming according to embodiments herein.

FIG. 6 illustrates the principle of the method according to which the embodiments described above operates.

FIG. 6 shows the wavefront WF1 and WF2 of two following transmission events TX1 and TX2 are shown.

The example of FIG. 6 has been simplified by being limited to a special case in which the receive line RX considered is coincident with transmit center line TX1. The transmit aperture of the transmit beam TX2 has been shifted laterally to the right in respect to TX1 by a step corresponding to the dimension of four transducer elements 601 of a transducer array 600. It is presumed that the aperture of the transmit beam TX2 or the width of the transmit beam TX2 is such as to encompass the receive line RX and the reflecting point P.

The situation is illustrated in relation to the n-th transducer element as receiving element.

The two wavefronts WF1 and WF2 are in general not planar and a focus P on a receiving line coincident with the center line of the transmission beam the path TX1 is considered.

The line TX2 is the center line of the laterally shifted second transmit beam.

The echoes generated at P have to travel a path RX to reach the n-th transducer element. The Second transmit event generates a wavefront WF2 which reaches the point with a different phase due to the lateral shift of the transmit beam of the transmit event TX2.

As it appears clearly, the receive multiline beamforming delays are defined by the geometry determined by the position of each focus points along each line at each line location relatively to the position of the transducer elements of the transducer array.

Figure 3B:
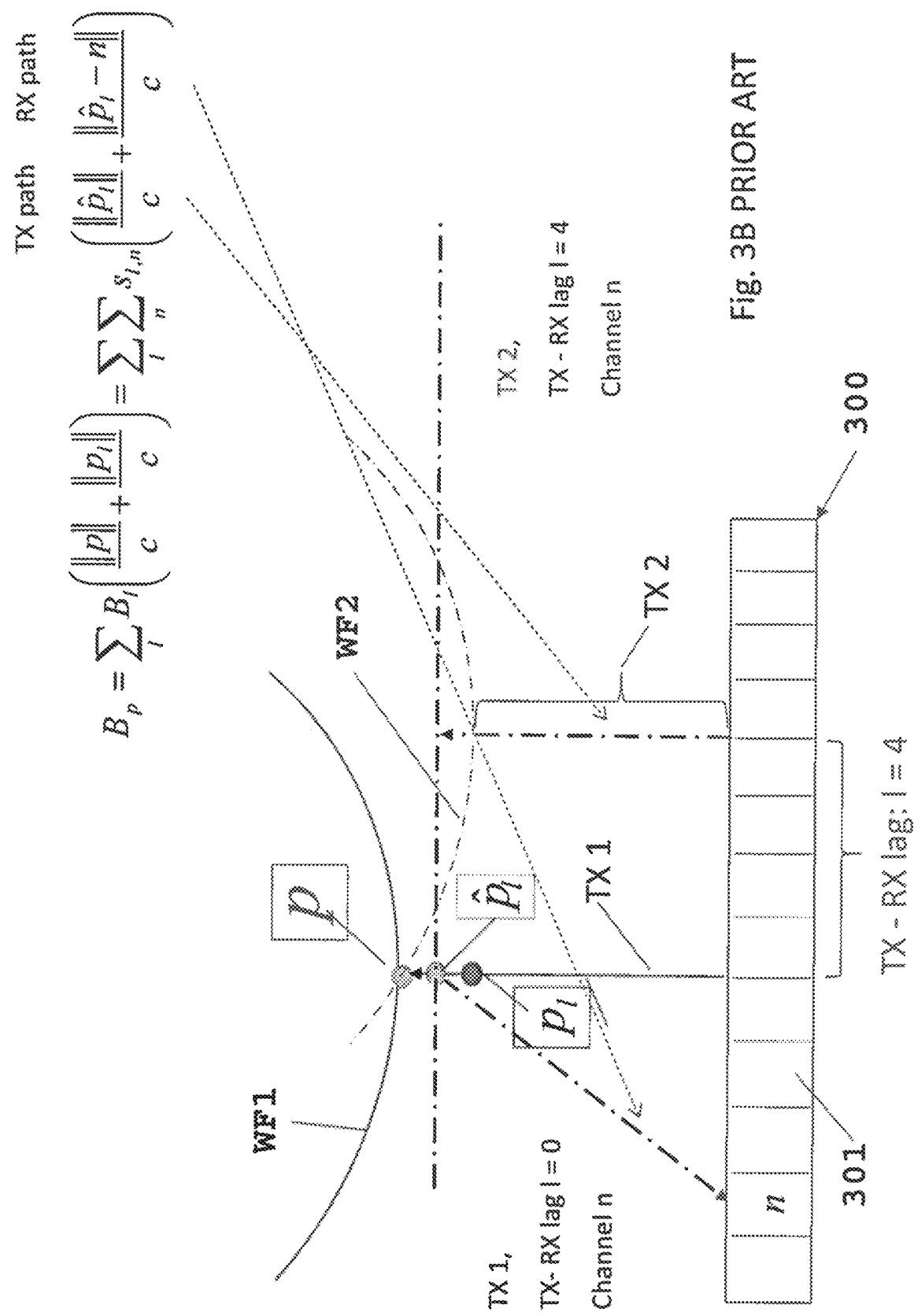
FIG. 3B illustrates with a diagram according to FIG. 3A the effect of the delay and phase shift correction applied by the prior art methods for carrying out retrospective transmit beamforming.

The equalization process would require to compensate for the delay of the transmit beam having the wavefront WF2 in reaching the focus points P on the corresponding line. In FIGS. 3A and 3B this phase shift is defined as RTB delay and is represented by the difference 320 in position of the focus point P of the transmit beam TX1 and the point P1. This situation apply here identically.

Considering $B_p$ the beam signal related to focal point p and $S_{l,n}(t)$ the signal at the probe channel n, i.e. at the n-th transducer element of the transducer array 600, which is related to a difference "l" in line position between the transmit center line of a second or following transmit beam TX2 and a receive line RX on which the focus point P lies, then the beam signal can be described by the following equation:

$$B_p = \sum_l \sum_n s_{l,n}\left(\frac{\|p - n\|}{c} + \frac{\|p_l\|}{c}\right)$$

In which:
the term $$\frac{\|p - n\|}{c}$$

is the path of the receive signal contribution to the n-th transducer element 701 of the transducer array 600.
The term $$\frac{\|p_l\|}{c}$$

is the path of the transmit beam TX2 along the centerline of the said transmit beam when the wavefront WF2 reaches the focus point P.
And wherein:
c is the speed of sound;
n being the number identifying the transducer elements of the array;
l defining the lateral shift of a transmit beam relatively to a receive line RX.
P are the coordinates of the focus point p;
$P_1$ are the coordinates of the point $P_1$.
Expanding the above equation the following equation is obtained:

$$B_p = \sum_l \sum_n s_{l,n}\left(\frac{\|p\|}{c} + \frac{\|p - n\|}{c} + \frac{\|p_l\|}{c} - \frac{\|p\|}{c}\right)$$

In which
The term $$\frac{\|p\|}{c} + \frac{\|p - n\|}{c}$$

corresponds to the beamforming or focalization delay to be applied to each of the n transducer elements 601 of the transducer array;
The term $$\frac{\|p_l\|}{c} - \frac{\|p\|}{c}$$

defining the delay in reaching the point p of the wave front WF2 of the transmit beam TX2 according to the l-th shift of the transmit aperture relatively to the transmit beam focused at p in the transmit event TX1: Thus the above term is the RTB delay to be applied for equalizing the phase shift between the receive signals from the focus point P on the receive line RX when combining the receive signals along said common line position RX originated by the two transmit events TX1 and TX2 the corresponding transmit beams being differently laterally shifted in relation to the said receive line position RX (in the example l=0 for TX1 and l=4 for TX2).

It has to be noted that in the present example of the method according to embodiments herein the Phase shift of the wave fronts of differently laterally shifted transmit beams reaching a focus point P along a common receive line position RX are exactly compensated so that no signal attenuation or cancellation is caused when combining the receive signals along the common line opposition together because the phases of the transmit beams are exactly synchronised.

A comparison with the prior art methods, the result of which is illustrated in FIG. 4, shows that while the effect of the equalisation according to the prior art is equivalent to focalize at a point $\hat{p}_1$ half way between point p and point $p_1$, the phase shift equalisation according to embodiments herein which is carried out contemporaneously with the realigned signal contributions by means of the beamforming delays provides for an exact focussing on the focus target point P.

FIG. 10 shows a simplified diagram of the method according to an embodiment.

Four different main phases are provided in the embodiment of FIG. 10.

A first phase 1000 relates to receipt of the receive signals following a multiline transmission mode, a processing of the receive signals in order to generate beamformed receive line data which contemporaneously have been subjected to a phase shift equalization related to the difference between receive line position relatively to the transmit beam aperture. During this phase also apodization weights are applied to the receive signals and the single channel contribution for each receive line position are summed for generating the said receive line signals.

In a following phase 1010, according to the embodiment described in FIG. 5 weights are applied to each of the k receive lines corresponding to a transmit beam line TX, i.e. falling within the aperture or width of the transmit beam TX. All the said selected receive line signals are stored in a memory.

The following phase 1020 provides for generating image line data by summing together a number R of co-aligned receive line signals in order to generate for every receive line position a Beamformed data.

In the phase 1000 at step 1001 receive data is received by the transducer elements of the transducer array of a probe for a number of focus points or pixels (numpoint) distributed over a target region or ROI. The target region or ROI may be mono-dimensional, bi-dimensional, three-dimensional or four-dimensional.

The receive signals are related to echoes generated by a multiline technique consisting in a plurality of transmit events each one comprising at least a transmit beam. Each transmit beam having a certain aperture or width encompassing a plurality of receive lines having different line positions each receive line comprising a number of focus points or pixels. The transmit beam of each transmission event covering a certain width of the ROI and the transmit beams of each following transmit event of the said plurality of transmit events being laterally shifted for a certain lateral displacement relatively to the previous transmit event. The lateral displacement being such that each receive line position falls within the width of the transmit beams of two or more following transmit events.

Thus each transmit event provides receive line signals along a common receive line position which receive line signals have to be coherently summed in order to obtain image data along the said receive line position or line of sight.

At step 1002 RTB delays (phase shift equalization delays) related to each receive line position of the number of receive line positions encompassed by the transmit beam width are summed and the delay resulting from this sum is applied al step 1003 to the receive signal contribution of each channel (transducer element) for each of the receive line positions falling within the width of the transmit beams.

At step 1004 apodization weights are applied by multiplication to the received signal contributions to which the summed RTB delays and beamforming delays has been applied at the previous step 1003.

For each of the receive line positions encompassed by the transmit beam width, the receive signal contributions from each channel to which the RTB delay and the beamforming delay has been applied at 1003 and to which the apodization weights has been applied at 1004 are summed together at 1005.

In the following phase 1010 to the receive line signals related to each receive line position or viewline encompassed by the transmit beams at step 1011 a RTB data weight is applied by multiplication of this weight.

At step 1012 each receive line signal is stored in a memory.

At phase 1020 a summation step 1021 is carried out by which the receive line signals falling on a common receive line or viewline position and deriving from different transmission event are coherently summed together forming beamformed image line data along each of a different view line or line of sight. The said number of view lines covering at least a part of the entire target region or one or more particular ROI's in this target region.

Figure 11:
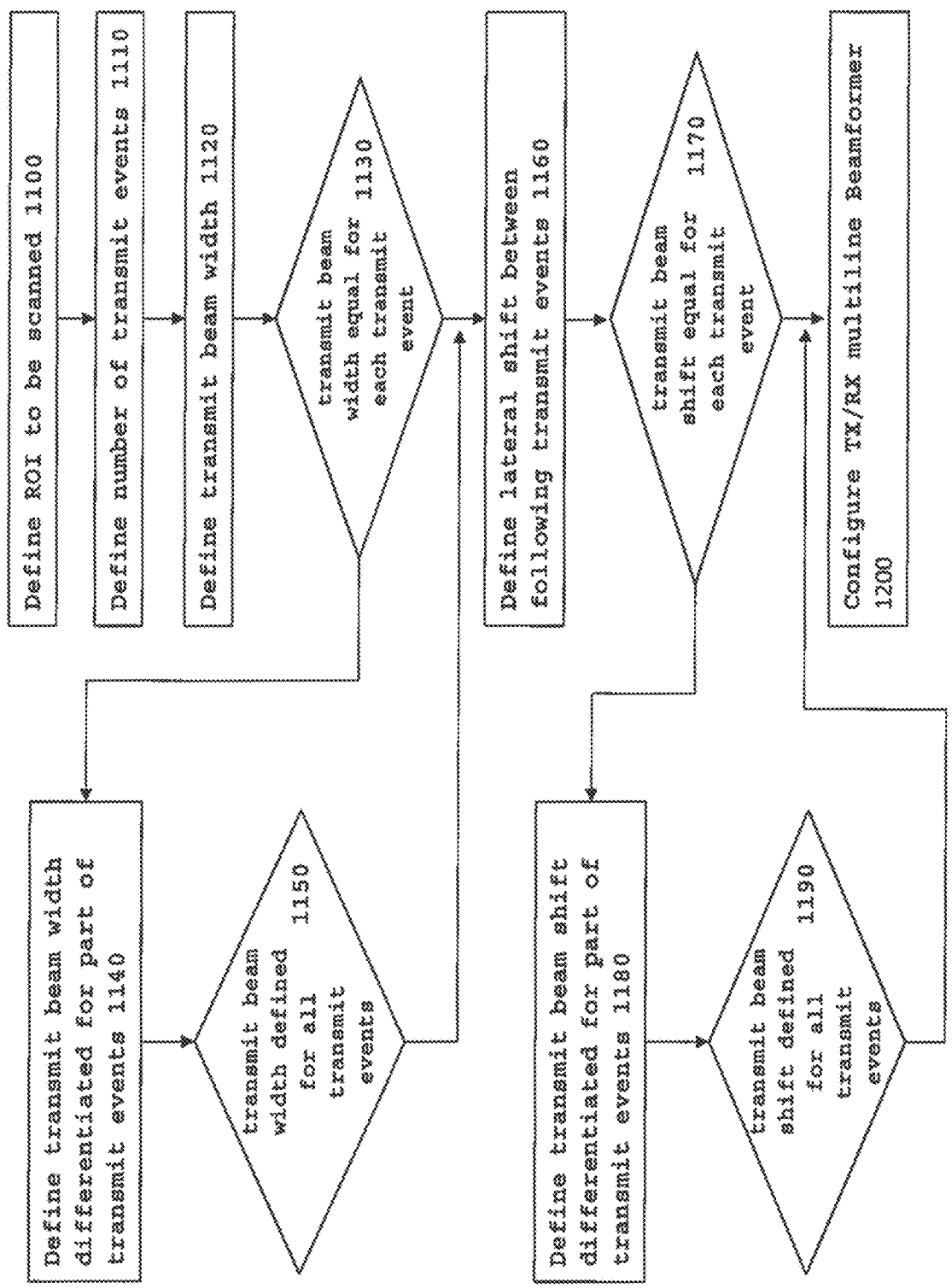
FIG. 11 is a flux diagram of the method according to a further embodiment.

According to a further embodiment illustrated in FIG. 11, the present RTB beamforming method may provide steps of selecting the parameters for the transmit events for scanning the target region.

A ROI may be selected at step 1100.

According to an embodiment a step 1110 of choosing the number of transmit events is provided. Optionally a steps 1120 is provided for defining the transmit beam aperture or width for each transmit event. Optionally 1130 the said transmit beam aperture or width may be different 1140 and 1150 for at least a part of the said transmit beam events.

According to an embodiment the method further comprises the step 1160 of defining the lateral shift between following transmit beam events. Optionally 1170 said step of lateral shift may be different 1180, 1190 for at least part of the transmit beam events.

According to still another embodiment, following the selection of the transmit beams an activation scheme of the multiline processors of the multiline beamformer is defined according to which the number of multiline processor which is activated corresponds to the number of receive lines falling within the width of the transmit beam which is represented by the step 1200 of configuring the TX/RX beamformer according to the selected parameters.

According to an embodiment an ultrasound system is provided comprising a user interface for inputting data, the said user interface sending input data to a processor which provides for configuring the transmit and the receive beamformer according to the input data.

According to an embodiment the said input data comprise the number of transmit events. Optionally the said input data comprises the transmit beam aperture or width for each transmit event.

According to an embodiment the said input data comprises the lateral shift between following transmit beam events.

According to an embodiment illustrated in FIG. 1A the input data interface 114 cooperates with the CPU 112 for inputting the various commands and setting parameters for controlling the ultrasound system.

CPU112 configures the different units according to the inputted parameters. Firing protocols are governed by the sequencer controller 110 by which applies the input data relating to the number of transmit events and/or the transmit beam aperture or width for each transmit event and/or the lateral shift between following transmit beam events.

Figure 7:
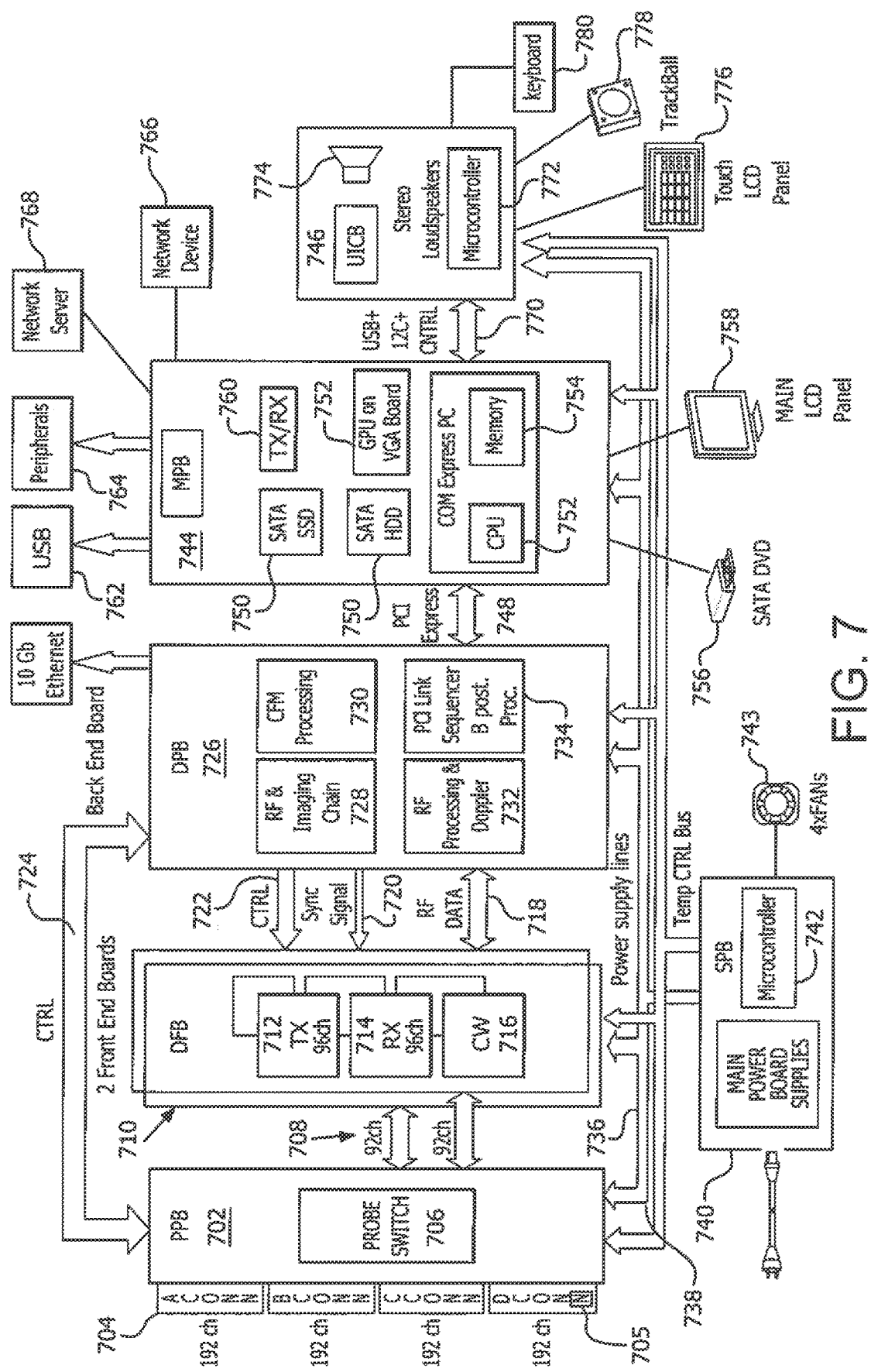
FIG. 7 illustrates a block diagram of an ultrasound system formed in accordance with an alternative embodiment.

FIG. 7 illustrates a block diagram of an ultrasound system formed in accordance with an alternative embodiment. The system of FIG. 7 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a selected one of the connection ports 704. The connect signal may be generated by the probe when power is initially supplied to the probe when coupled to the connection port 704. Additionally, or alternatively, each connection port 704 may include a sensor 705 that detects when a mating connection on a cable of a probe has been interconnected with the corresponding connection port 704. The sensor 705 provides signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 724. A power supply line 736 provides power from a power supply 740 to the various components of the system, including but not limited to, the probe interconnection board (PIB) 702, digital front end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally, or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front end boards 710 may convert the RF ultrasound data to I,Q data pairs which are then passed to the digital processing board 726.

The digital processing board 726 includes an RF and imaging module 728, a color flow processing module 730, an RF processing and Doppler module 732 and a PCI link module 734. The digital processing board 726 performs RF filtering and processing, processing of black and white image information, processing in connection with color flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 performs various ultrasound related imaging, such as B mode related image processing of the RF data. The RF processing and Doppler module 732 convert incoming RF data to I,Q data pairs, and performs Doppler related processing on the I, Q data pairs. Optionally, the imaging module 728 may perform B mode related image processing upon I, Q data pairs. The CFM processing module 730 performs color flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 8:
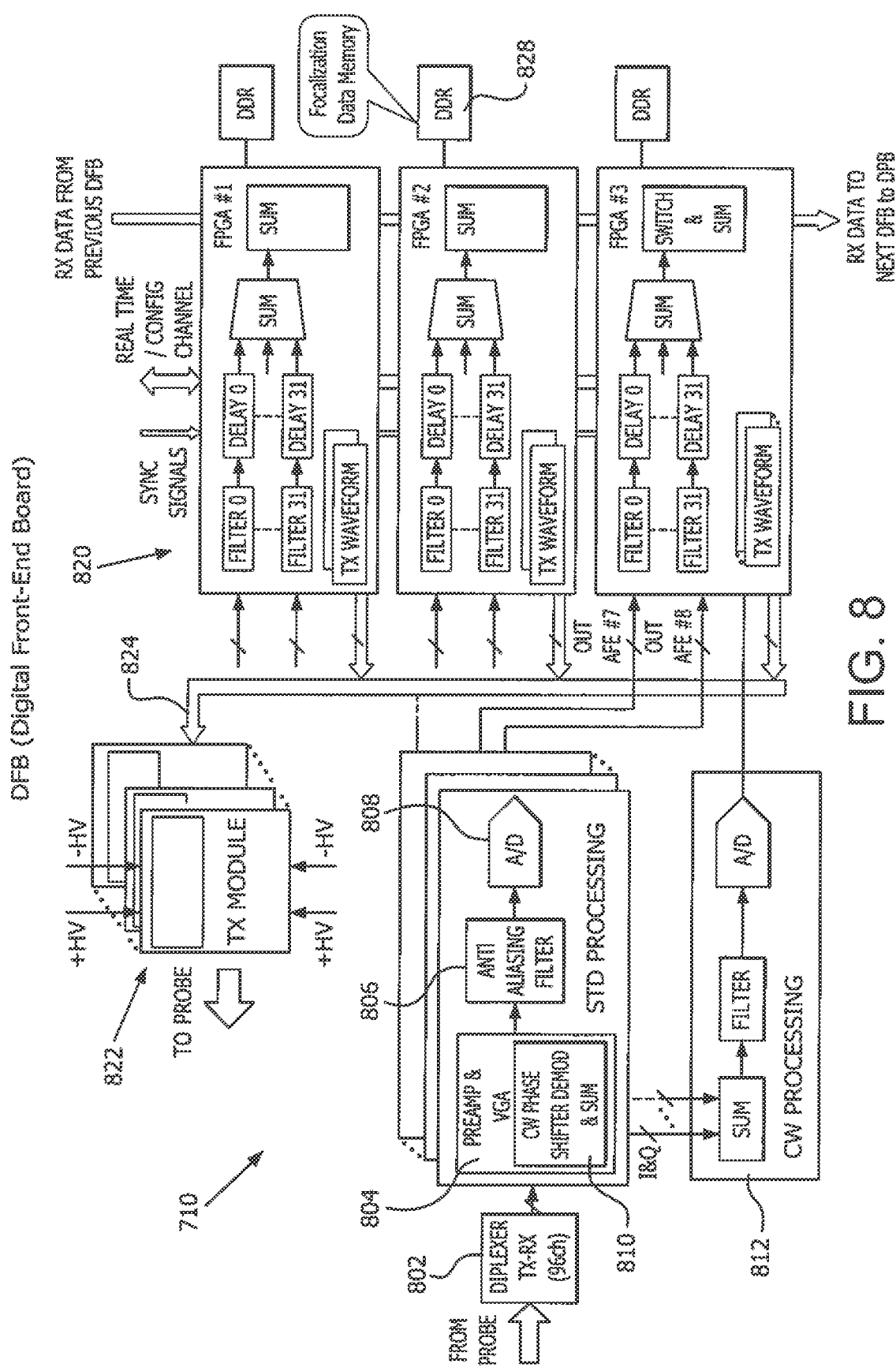
FIG. 8 illustrates a block diagram of a portion of the digital front-end boards.

FIG. 8 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering.

According to an embodiment, the retrospective transmit beam focusing may be applied to the RF data directly acquired by the system or to transformed data according to different transformations as for example as a phase/quadrature (I/Q) transformation, or similar.

In the embodiment of FIG. 8 an example of the said transformation of the RF data is disclosed According to this example, the output of the filter 806 is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF receive signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 826 (FIG. 7). The FPGAs receive focalization data from memories 828. The focalization data is utilized to manage the filters, delays and summing operations performed by the FPGAs in connection with beamforming. The beamformed RF or I/Q data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

Figure 9:
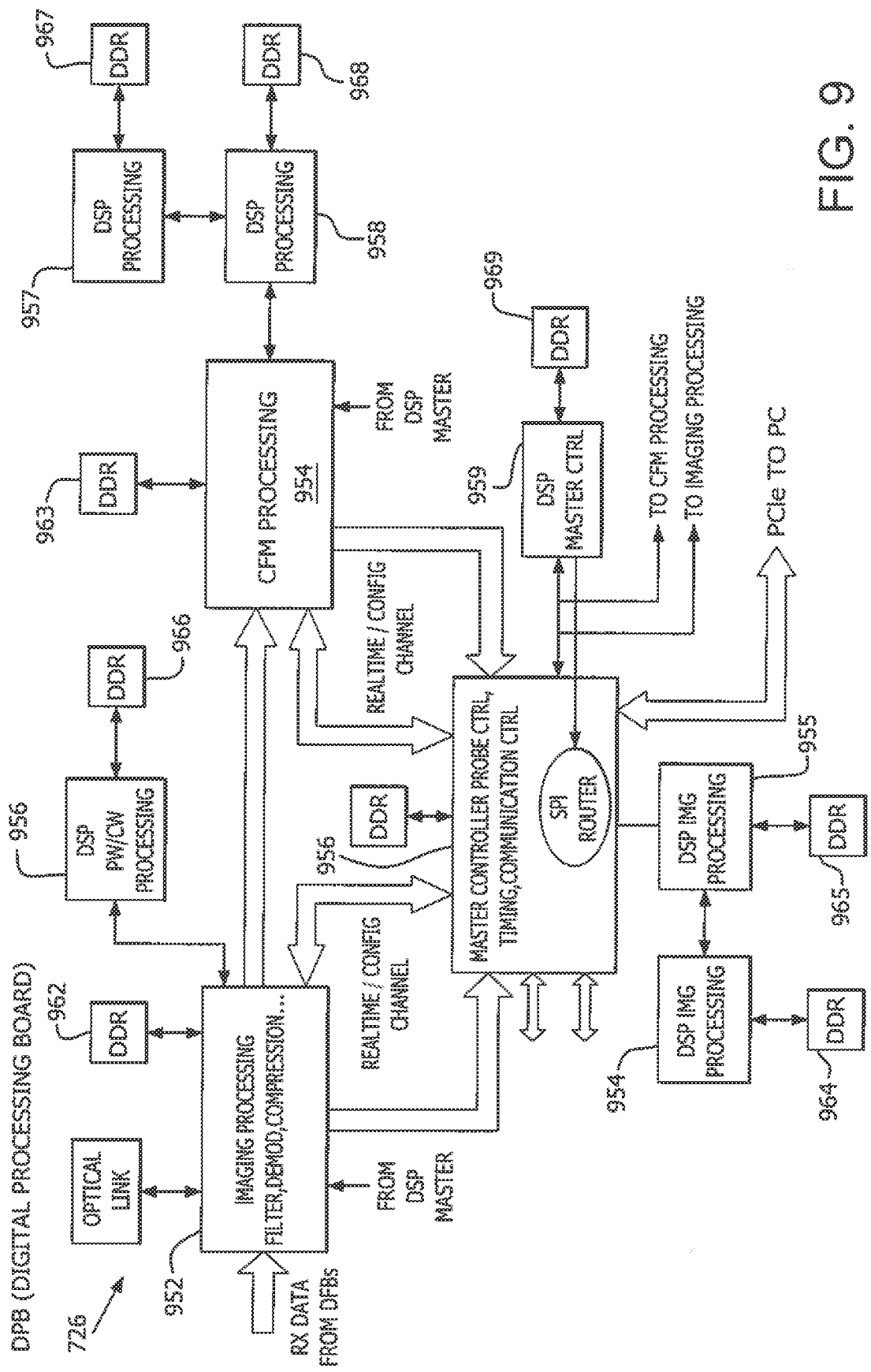
FIG. 9 illustrates a block diagram of the digital processing board.

FIG. 9 illustrates a block diagram of the digital processing board 726 implemented in accordance with embodiments herein. The digital processing board 726 includes various processors 952-959 to perform different operations under the control of program instructions saved within corresponding memories see 962-969. A master controller 950 manages operation of the digital processing board 726 and the processors 952-959. By way of example, one or more processors as the 952 may perform filtering, the modulation, compression and other operations, while another processor 953 performs color flow processing. The master controller provides probe control signals, timing control signals, communications control and the like. The master controller 950 provides real-time configuration information and synchronization signals in connection with each channel to the digital front-end board 710.

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS., which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the present disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

According to an embodiment the width or aperture of the transmit and/or of the received beam may be changed as a function of different effects.

In a first case the width of the beam may be varied as a function of the motion of one or more objects in the images.

In combination or in alternative the width of the beam may be varied as a function of the imaging mode selected, such as for example B-mode of any of the different Doppler imaging modes.

As a further alternative, width of the ultrasound beam may be reduced or increased as a function of the desired tradeoff between frame rate and the depth of field.

Furthermore the above combination or alternatives can be also used for triggering a variation of the spacing between the transmit lines and/or the spacing of the receive lines.

Figure 12:
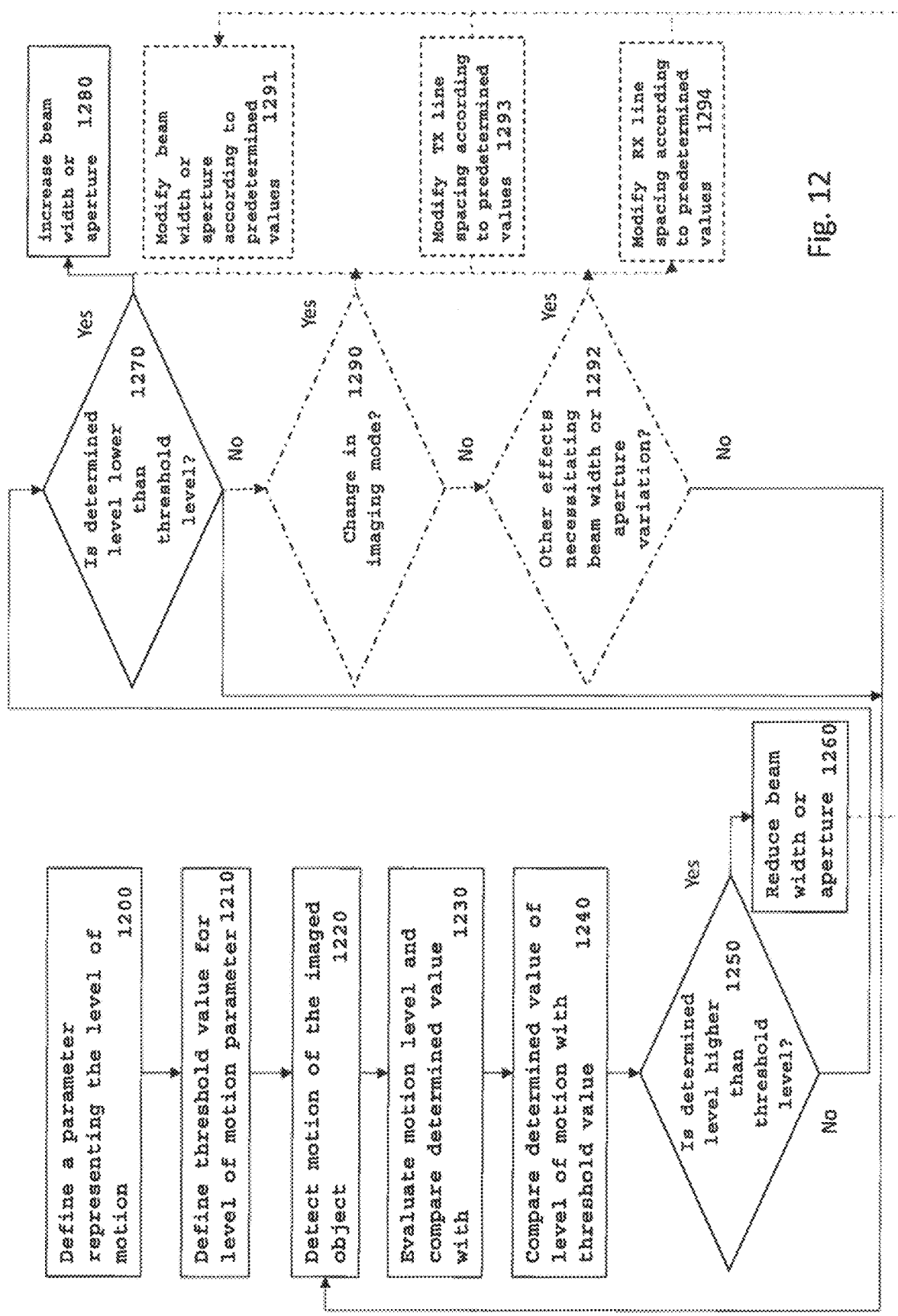
FIG. 12 is a flux diagram describing the method for changing the width or aperture of the ultrasound beam in case of motion, change in imaging mode or in other conditions.

According to the flux diagram of FIG. 12, an embodiment is represented in which the above variations of the beams width and/or of the spacing between transmit lines and/o the spacing between receive lines are provided. At step 1200 a parameter is defined which represents the level of motion. This can be done in several ways. One way is to correlate the pixel values of an identical or quite identical area of a sequence of image frames. The correlation factor can be defined as a parameter measuring the level of motion.

At step 1210 a threshold value for the level of motion parameter is defined. Detecting motion at step 1220 and determining the corresponding value of the parameter representing the level of motion at step 1230 leads to step 1240. At this step the determined value of the level of motion parameter is compared with the threshold. If the result at 1250 indicates that the determined parameter is higher than the threshold, than at step 1260 the beam width is is reduced or the aperture is modified in the sense to encompass fewer lines. If the level of motion is lower than the threshold as indicated at step 1270, than the beam width is increased or the aperture is modified in roder to encompass a higher number of lines as indicated at step 1280.

If no motion is detected such that the determined level of motion is identical within a certain range of tolerance with the value of the threshold, the motion detection cycle goes on. In FIG. 12 with discontinuous lines there are shown further steps which might be optional in combination with the one described above or even alternative to the one described above.

Alternatively or in combination with the increase or decrease of the beam aperture or width at steps 1260 and 1280, also other parameters can be modified as indicated by the steps 1291, 1293 and 1294. In this case the fact that these steps may be provided or not is indicated by discontinuous lines. Step 1291 provides for having predetermined values to modify the width or aperture of the beam. Step 1293 and 1294 provides for modifying the spacing respectively between transmit lines and receive lines. Both steps may be executed alternatively to one another or to the increase or decrease of the beam aperture or width or in combination one with the other or together or separately in combination with the step of increasing or reducing the beam aperture or width.

Further possible steps consists for example of step 1290 in which the decision is taken if the imaging mode has been changed and if different beam width are set for different imaging modes, then if the answer is affirmative, at step 1291 the width of the beam is changed according to the predetermined settings for the chosen imaging mode. Similarly as for the motion detection case, also in changing imaging mode the steps 1293 and 1294 of modifying the spacing between respectively the transmit and the receive lines are optionally carried out in any combination or sub combination as already disclosed in relation to the motion detection case.

At step 1292 the optional step is provided to determine if there are further effects which may be compensated or achieved by modifying the beam width or aperture. An non exhaustive and limiting example may be a tradeoff between frame rate and depth of field.

Also in this case the beam width or aperture is modified as indicated at step 1280 and the other optional steps relating to the line spacing variation as shown by 1293 and 1294 may be carried out in any combination and sub combination as disclosed for the motion detection case. If no modification of the beam width is carried out, then the cycle of determining motion is repeated.

In FIG. 1A, with dotted lines there are shown a variant embodiment of an ultrasound system which is configured to carry out the above described method.

Additionally, to the above description of figure LA, the system comprises a motion detector unit 161. The motion detector unit is connected to the Image scan converter 107 for carrying out a correlation technique between subsequent image frame or of same areas of the said image frames.

Different embodiments may be provided in which motion detector may be carried out at the stage of the radiofrequency signals generated by the reflected beams on the transducers of the probe 101.

An ultrasound beam width or aperture controller 160 may receive directly a control signal for automatically modifying the width of the ultrasound beam as a function of the detected motion. In this case the motion detector 161 can be a processing unit executing a motion detector program coding the instructions for determining a parameter representing the level of the detected motion. This data can be used by the motion detector 161 or by the controller 162 for causing the variation of the beam width.

Also with dotted lines two controllers 158 and 159 are shown respectively for setting the receive line spacing of the receive lines encompassed by the beam width and the transmit line spacing. The motion detection unit 161 is also connected to these controllers 158 and 159 for modifying the line spacing as a function of the motion of the imaged objects Alternatively, or in combination, the motion detector 161 may transmit the data about motion detection to the CPU 112. In this case the computation and the generation of the signal driving the controllers 1160, 158 and 159 for modifying the width or aperture of the beam and/or the receive line spacing and/or the transmit line spacing may be carried out by the CPU 112 executing a program coding the instruction for configuring the CPU 112 to carry out the said functions.

As a further alternative the CPU 112 may control the user interface 114 for providing input organs for manual control of the width of the beam by manually inputting the setting of one or more of the controllers 158, 159 and 160.

Similarly the unit 106 for carrying out the different imaging modes may be either directly connected to the controller 158, 159 and 160 respectively for setting the receive line spacing, the transmit line spacing and for modifying automatically the width or the aperture of the beam as a function of the imaging mode, or this variation may be controlled manually by the user interface, providing a selector of the imaging mode and/or a manual control organ of one or more of the controllers 158, 159, 160.

It has to be noted that the unit described may be in the form of programs coding the instructions for processors to carry out the functions according to the described method in any of its variant embodiment. In this condition, the ultrasound system for carrying out variation of the beam width or aperture may be also realized as in the embodiment of FIGS. 7 to 9.

The invention claimed is:

1. A method for performing retrospective dynamic transmit focusing beamforming for ultrasound signals, the method comprising:
    a) transmitting a plurality of transmit beams from an array transducer, each transmit beam being centered at a different position along the array and each transmit beam having a width or an aperture encompassing a plurality of laterally spaced line positions, each transmit beam width or aperture overlapping at least partially the width or the aperture of the immediately adjacent transmit beam or of more laterally spaced transmit beams;
    b) receiving echo signals with the array transducer;
    c) processing the echo signals received in response to one transmit beam to produce a plurality of receive lines of echo signals at the laterally spaced line positions within the width or the aperture of the transmit beam;
    d) repeating the receiving step b) and the processing step c) for the additional transmit beams of the plurality of transmitted transmit beams of step a);
    e) equalizing the phase shift variance among receive lines at a common line position resulting from transmit beams of different transmit beam positions;
    f) combining echo signals of receive lines from different transmit beams which are spatially related to a common line position to produce image data; and
    g) producing an image using the image data;
    and in which the step e) of equalizing the phase shift is carried out contemporaneously within the processing step c) and d) by applying to each of the contribution of the receive signals at transducer elements of the array from each reflecting or focus point at a common line position a combined delay parameter determined by a sum of
        a focalization delay consisting in a delay of each receive signal contribution received b the transducer elements realigning the time of arrivals of the said signal contribution from a receive signal from a reflecting point or focus at the said transducer elements, and
        a phase shift equalization delay determined by the phase shift between the wave fronts of the different transmit beams centered at different transmission lines at the said reflecting point or focus;
    wherein for each receive signal along a receive line position, the focalization delays and the base shift equalization delays are applied to the receive signal contributions of the transducer elements or channels before their summation.

2. The method according to claim 1, wherein for each transmission of a transmit beam with a certain aperture, the received echoes are processed by a set of beamformer processors, each one related to a different line of sight;
    each beamformer being characterized by a set of dynamic delays and optionally by a set of apodization weights, which are different for each beamformer processor.

3. The method according to claim 1, wherein, after beamforming, each line of sight is stored in a buffer and along with subsequent insonifications, receive lines corresponding to the same line positions are coherently summed together to produce a final beamformed line with uniform spatial resolution.

4. A method according to claim 1, wherein apodization weights are applied to each receive signal contribution from each channel of each of the said beamforming processors.

5. A method according to claim 1, further comprising applying a further weight to the receive line signals along different line positions encompassed by the transmit beam aperture or width.

6. A method according to claim 1 further comprising:
    Determining motion of one or more objects in the imaged region;
    Modifying the width or the aperture of the transmit or of the received beams as a function of the motion detected.

7. A method according to claim 1 further comprising:
    Determining a certain transmit or receive beam aperture or width related to an imaging mode;
    Selecting an imaging mode and manually or automatically setting the determined beam aperture or width for the said imaging mode.

8. A method according to claim 1 further comprising:
    Determining predefined imaging conditions;
    Determining a predefined width or aperture or a predefined range of width or of the apertures for each the said predefined imaging conditions;
    Selecting an imaging condition and automatically or manually setting the corresponding width or aperture of the beam.

9. A method according to claim 1 further comprising:
    Determining motion of one or more objects in the imaged region;
    Modifying the spacing between transmit lines and/or the number of lines encompassed by the transmit beam aperture as a function of the motion detected.

10. A method according to claim 1 further comprising:
    Determining a certain transmit line spacing related to an imaging mode;
    Selecting an imaging mode and manually or automatically setting the predetermined transmit line spacing and/or the said number of lines for the said imaging mode.

11. A method according to claim 1 further comprising:
    Determining predefined imaging conditions;
    Determining a predefined transmit line spacing and/or a predefined number of lines for each the said predefined imaging conditions;
    Selecting an imaging condition and automatically or manually setting the corresponding transmit line spacing and or the corresponding number of lines.

12. A method according to claim 1 further comprising:

Determining motion of one or more objects in the imaged region;

Modifying the spacing between receive lines and/or the number of lines encompassed by the beam aperture as a function of the motion detected.

13. A method according to claim 1 further comprising:

Determining a certain receive line spacing and or a certain receive number of lines related to an imaging mode;

Selecting an imaging mode and manually or automatically setting the predetermined receive line spacing and/o the said number of lines for the said imaging mode.

14. A method according to claim 1 further comprising:

Determining predefined imaging conditions;

Determining a predefined receive line spacing and/or a predefined number of receive lines encompassed by the receive beam for each the said predefined imaging conditions;

Selecting an imaging condition and automatically or manually setting the corresponding receive line spacing and/or the said receive line number.

\* \* \* \* \*